(12) United States Patent
Batra et al.

(10) Patent No.: US 7,166,704 B2
(45) Date of Patent: Jan. 23, 2007

(54) ANTIBODIES IMMUNOLOGICALLY SPECIFIC FOR PD2, A PROTEIN THAT IS AMPLIFIED AND OVEREXPRESSED IN PANCREATIC CANCER

(75) Inventors: Surinder K. Batra, Omaha, NE (US); Michael A. Hollingsworth, Omaha, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 195 days.

(21) Appl. No.: 10/721,553

(22) Filed: Nov. 25, 2003

(65) Prior Publication Data

US 2005/0032079 A1 Feb. 10, 2005

Related U.S. Application Data

(62) Division of application No. 09/647,143, filed on Sep. 27, 2000, now Pat. No. 6,680,196.

(60) Provisional application No. 60/079,649, filed on Mar. 27, 1998.

(51) Int. Cl.
*C07K 16/00* (2006.01)
(52) U.S. Cl. .................. 530/387.7; 530/387.1; 530/530; 435/7.1
(58) Field of Classification Search ............. 530/387.1, 530/350, 387.7
See application file for complete search history.

(56) References Cited

U.S. PATENT DOCUMENTS 5,932,442 A * 8/1999 Lal et al. .................... 435/69.1

OTHER PUBLICATIONS

Sato et al (American Society of Plant Biologists, 1997, Abstract # 90).*
Sigma Immuno Chemicals 1993 Catalog (16 pages).*
Berger et al. Guide to molecular cloning techniques 431-443 1987.*
Sambrook et al. Molecular cloning 1989 pp. 1145-1147.*
Ngo et al. Computational complexity, protein structure prediction, and the levinthal paradox pp. 491-495 1994.*
Bowie et al. Deciphering the message in protein sequences: tolerance to amino acid substitutions pp. 1306-1309 vol. 247 1990.*
Results were produced by the gencore software version 4.5 1993-2000 p. 1-2.*
Batra, S.K. et al., "Biology of Disease—Oncogenes and Anti-oncogenes in Human Central Nervous System Tumors"; Laboratory Investigation, 71(5): 621-637 (1994).
Batra, S.K. et al., "Isolation and Characterization of a Complementary DNA (PD-1) Differentially Expressed by Human Pancreatic Ductal Cell Tumors"; Cell Growth & Differentiation, 2: 385-390 (1991).
Griffin, C.A. et al. "Consistent Chromosome Abnormalities in Adenocarcinoma of the Pancreas"; Cancer Research, 55: 2394-2399 (1995).
Mackay, A.M. et al. "Molecular Analysis of the INCENPs (Inner Centromere Proteins): Separate Domains Are Required for Association with Microtubules During Interphase and with the Central Spindle During Anaphase"; The Journal of Cell Biology, 123(2): 373-385 (1993).

* cited by examiner

*Primary Examiner*—Jeffrey Siew
*Assistant Examiner*—Laura Goddard
(74) *Attorney, Agent, or Firm*—Dann Dorfman Herrell and Skillman; Kathleen D. Rigaut

(57) ABSTRACT

A human nucleic acid, PD2, its encoded protein and antibodies immunologically specific thereto are disclosed herein. The expression of the disclosed PD2 gene plays a key role in the regulation of differentiation and in the maintenance of the neoplastic state. The PD2 gene and its encoded protein represent valuable therapeutic targets in the differential diagnosis and therapy of pancreatic adenocarcinomas.

9 Claims, 17 Drawing Sheets

Figure 2

```
TTCTCGCCCGCCCACCTCATCTCAACCCACTTTCCGCGGGGAGCGGCGCCAAGCTGGGCC
TTCCTCGGATCAGGCGTCCCCTGAAGTCGGCACGCCCTCTGCGTCCCCCTTCGGTCCCG
CTAGGACCCCGTCCGGGCTGCCGTCGCCTCGTCGCTATGGCGCCCACCATCCAGACCCAG
                                  M  A  P  T  I  Q  T  Q
GCCCAGCGGGAGGATGGCCACAGGCCCAATTCCCACCGGACTCTGCCTGAGAGGTCTGGA
 A  Q  R  E  D  G  H  R  P  N  S  H  R  T  L  P  E  R  S  G
GTGGTCTGCCGAGTCAAGTACTGCAATAGCCTCCCTGATATCCCCTTCGACCCCAAGTTC
 V  V  C  R  V  K  Y  C  N  S  L  P  D  I  P  F  D  P  K  F
ATCACCTACCCCTTCGACCAGAACAGGTTCGTCCAGTACAAAGCCACTTCCTTGGAGAAA
 I  T  Y  P  F  D  Q  N  R  F  V  Q  Y  K  A  T  S  L  E  K
CAGCACAAACATGACCTCCTGACTGAGCCAGACCTGGGGGTCACCATCGATCTCATCAAT
 Q  H  K  H  D  L  L  T  E  P  D  L  G  V  T  I  D  L  I  N
CCTGACACCTACCGCATCGACCCCAATGTTCTTCTAGATCCAGCTGATGAGAAACTTTTG
 P  D  T  Y  R  I  D  P  N  V  L  L  D  P  A  D  E  K  L  L
GAAGAGGAGATTCAGGCCCCCACCAGCTCCAAGAGATCCCAGCAGCACGCGAAGGTGGTG
 E  E  E  I  Q  A  P  T  S  S  K  R  S  Q  Q  H  A  K  V  V
CCATGGATGCGAAAGACAGAGTACATCTCCACTGAGTTCAACCGTTATGGCATCTCCAAT
 P  W  M  R  K  T  E  Y  I  S  T  E  F  N  R  Y  G  I  S  N
GAGAAGCCTGAGGTCAAGATTGGGGTTTCTGTGAAGCAGCAGTTTACCGAGGAAGAAATA
 E  K  P  E  V  K  I  G  V  S  V  K  Q  Q  F  T  E  E  E  I
TACAAAGACAGGGATAGCCAGATCACAGCCATTGAGAAGACTTTTGAGGATGCCCAGAAA
 Y  K  D  R  D  S  Q  I  T  A  I  E  K  T  F  E  D  A  Q  K
TCAATCTCACAGCATTACAGCAAACCCCGAGTCACACCGGTGGAGGTCATGCCTGTCTTC
 S  I  S  Q  H  Y  S  K  P  R  V  T  P  V  E  V  M  P  V  F
CCAGACTTTAAGATGTGGATCAATCCATGTGCTCAGGTGATCTTTGACTCAGACCCAGCC
 P  D  F  K  M  W  I  N  P  C  A  Q  V  I  F  D  S  D  P  A
CCCAAGGACACGAGTGGTGCAGCTGCGTTGGAGATGATGTCTCAGGCCATGATTAGGGGC
 P  K  D  T  S  G  A  A  A  L  E  M  M  S  Q  A  M  I  R  G
ATGATGGATGAGGAAGGGAACCAGTTTGTGGCCTATTTCCTGCCTGTAGAAGAGACGTTG
 M  M  D  E  E  G  N  Q  F  V  A  Y  F  L  P  V  E  E  T  L
AAGAAACGAAAGCGGGACCAGGAGGAGGAGATGGACTATGCACCAGATGATGTGTATGAC
 K  K  R  K  R  D  Q  E  E  E  M  D  Y  A  P  D  D  V  Y  D
TACAAAATTGCTCGGGAGTACAACTGGAACGTGAAGAACAAAGCTAGCAAGGGCTATGAG
 Y  K  I  A  R  E  Y  N  W  N  V  K  N  K  A  S  K  G  Y  E
GAAAACTACTTCTTCATCTTCCGAGAGGGTGACGGGGTTTACTACAATGAGTTGGAAACC
 E  N  Y  F  F  I  F  R  E  G  D  G  V  Y  Y  N  E  L  E  T
AGGGTCCGCCTTAGTAAGCGCCGGGCCAAGGCTGGGGTTCAGTCAGGCACCAACGCCCTG
 R  V  R  L  S  K  R  R  A  K  A  G  V  Q  S  G  T  N  A  L
CTTGTGGTCAAACATCGGGACATGAATGAGAAGGAACTGGAAGCTCAGGAGGCACGGAAG
 L  V  V  K  H  R  D  M  N  E  K  E  L  E  A  Q  E  A  R  K
GCCCAGCTAGAAAACCACGAACCGGAGGAGGAAGAGGAAGAGGAGATGGAGACAGAAGAG
 A  Q  L  E  N  H  E  P  E  E  E  E  E  M  E  T  E  E
AAAGAAGCTGGGGGCTCAGATGAGGAGCAGGAGAAGGGCAGCAGCAGTGAGAAGGAGGGC
 K  E  A  G  G  S  D  E  E  Q  E  K  G  S  S  S  E  K  E  G
AGTGAAGATGAGCACTCGGGCAGCGAGAGTGAACGGGAGGAAGGTGACAGGGACGAGGCC
 S  E  D  E  H  S  G  S  E  S  E  E  G  D  R  D  E  A
AGTGACAAGAGTGGCAGTGGTGAGGACGAGAGCAGCGAGGATGAGGCCCGGGCTGCCCGT
 S  D  K  S  G  S  G  E  D  E  S  S  E  D  E  A  R  A  A  R
GACAAAGAGGAGATCTTTGGCAGTGATGCTGATTCTGAGGACGATGCCGACTCTGATGAT
 D  K  E  E  I  F  G  S  D  A  D  S  E  D  D  A  D  S  D  D
GAGGACAGAGGACAGGCCCAAGGTGGCAGTGACAATGATTCAGACAGCGGCAGCAATGGG
 E  D  R  G  Q  A  Q  G  G  S  D  N  D  S  D  S  G  S  N  G
GGTGGCCAGCGGAGCCGGAGCCACAGCCGCAGCGCCAGTCCCTTCCCCAGTGGCAGCGAG
 G  G  Q  R  S  R  S  H  S  R  S  A  S  P  F  P  S  G  S  E
CACTCGGCCCAGGAGGATGGCAGTGAAGCTGCAGCTTCTGATTCCAGTGAAGCTGATAGT
 H  S  A  Q  E  D  G  S  E  A  A  A  S  D  S  S  E  A  D  S
GACAGTGACTGAGTCCCAGGGCATTCAGGGCTGGTTCAGACACCATTATTGTGAGCAGCA
 D  S  D  *
AAGCACTTTTCTAGTGGTCTGTTTGTGAGCCTTTCACTTGTTTGTTCCCCACCCCCAAAC
CTTTGCTGTTAATAAAGTCAACTTCTCTTTAAAAAAAAAAAAAAAAAAAAAAAAAAAAAA
AAAAAAAAAAAAAAAAAA
```

Figure 5

```
       Basic                    Helix                           Helix
A. SDRRSNKPIMEKRRRARINNCINEL ...loop... KADILEKIVKH..IQE
B. HRPNSHRTLPERSVVCRVKVC.NSL ...loop... KATSLEKQHKHDLITE
    *        *       ** **
```

Figure 6

A. SFGELALI..YGYPRAAITVK
B. YFGEIAIL..LNRPRAAITVV
C. FIGELGLFEGQERSRAKTAC
D. VYNELETRVRLSKRRAKAGV

SEQUENCE LISTING

```
<160> NUMBER OF SEQ ID NOS: 22

<210> SEQ ID NO 1
<211> LENGTH: 1937
<212> TYPE: DNA
<213> ORGANISM: Homo sapiens

<400> SEQUENCE: 1
ttctcgcccg cccacctcat ctcaacccac tttccgcggg gagcggcgcc aagctgggcc        60
ttcctcggat caggcgtccc ctgaagtcgg cacgcccctc tgcgtcccc  ttcggtcccg       120 ctaggacccc gtccgggctg ccgtcgcctc gtcgctatgg cgcccaccat ccagacccag       180
gcccagcggg aggatggcca caggcccaat tcccaccgga ctctgcctga gaggtctgga       240
gtggtctgcc gagtcaagta ctgcaatagc ctccctgata tccccttcga ccccaagttc       300
atcacctacc ccttcgacca gaacaggttc gtccagtaca aagccacttc cttggagaaa       360
cagcacaaac atgacctcct gactgagcca gacctggggg tcaccatcga tctcatcaat       420
cctgacacct accgcatcga ccccaatgtt cttctagatc cagctgatga gaaactttg        480 gaagaggaga ttcaggcccc caccagctcc aagagatccc agcagcacgc gaaggtggtg       540
ccatggatgc gaaagacaga gtacatctcc actgagttca accgttatgg catctccaat       600
gagaagcctg aggtcaagat tggggttct gtgaagcagc agtttaccga ggaagaaata        660
tacaaagaca gggatagcca gatcacagcc attgagaaga cttttgagga tgcccagaaa       720
tcaatctcac agcattacag caaacccga gtcacaccgg tggaggtcat gcctgtcttc       780
ccagacttta agatgtggat caatccatgt gctcaggtga tctttgactc agacccagcc       840
cccaaggaca cgagtggtgc agctgcgttg gagatgatgt ctcaggccat gattagggc        900 atgatggatg aggaagggaa ccagtttgtg gcctatttcc tgcctgtaga agagacgttg       960
aagaaacgaa agcgggacca ggaggaggag atggactatg caccagatga tgtgtatgac      1020
tacaaaattg ctcgggagta caactggaac gtgaagaaca aagctagcaa gggctatgag      1080
gaaaactact tcttcatctt ccgagagggt gacggggttt actacaatga gttggaaacc      1140
```

-continued

```
agggtccgcc ttagtaagcg ccgggccaag gctggggttc agtcaggcac caacgccctg    1200
cttgtggtca acatcggga catgaatgag aaggaactgg aagctcagga ggcacggaag    1260
gcccagctag aaaaccacga accggaggag aagaggaag aggagatgga dacagaagag    1320
aaagaagctg ggggctcaga tgaggagcag agaaagggca gcagcagtga aaggagggc    1380 agtgaagatg agcactcggg cagcgagagt gaacgggagg aaggtgacag ggacgaggcc    1440
agtgacaaga gtggcagtgg tgaggacgag agcagcgagg atgaggcccg ggctgcccgt    1500
gacaaagagg agatctttgg cagtgatgct gattctgagg acgatgccga ctctgatgat    1560
gaggacagag gacaggccca aggtggcagt gacaatgatt cagacagcgg cagcaatggg    1620
ggtggccagc ggagccggag ccacagccgc agcgccagtc ccttcccag tggcagcgag    1680 cactcggccc aggaggatgg cagtgaagct gcagcttctg attccagtga agctgatagt    1740
gacagtgact gagtcccagg gcattcaggg ctggttcaga caccattatt gtgagcagca    1800
aagcactttt ctagtggtct gtttgtgagc ctttcacttg tttgttcccc acccccaaac    1860
ctttgctgtt aataaagtca acttctcttt aaaaaaaaaa aaaaaaaaaa aaaaaaaaa    1920 aaaaaaaaaa aaaaaaa                                                    1937
```

<210> SEQ ID NO 2
<211> LENGTH: 531
<212> TYPE: PRT
<213> ORGANISM: Homo sapiens

<400> SEQUENCE: 2

```
Met Ala Pro Thr Ile Gln Thr Gln Ala Gln Arg Glu Asp Gly His Arg
  1               5                  10                  15

Pro Asn Ser His Arg Thr Leu Pro Glu Arg Ser Gly Val Val Cys Arg
             20                  25                  30

Val Lys Tyr Cys Asn Ser Leu Pro Asp Ile Pro Phe Asp Pro Lys Phe
         35                  40                  45

Ile Thr Tyr Pro Phe Asp Gln Asn Arg Phe Val Gln Tyr Lys Ala Thr
     50                  55                  60

Ser Leu Glu Lys Gln His Lys His Asp Leu Leu Thr Glu Pro Asp Leu
 65                  70                  75                  80

Gly Val Thr Ile Asp Leu Ile Asn Pro Asp Thr Tyr Arg Ile Asp Pro
                 85                  90                  95

Asn Val Leu Leu Asp Pro Ala Asp Glu Lys Leu Leu Glu Glu Glu Ile
            100                 105                 110

Gln Ala Pro Thr Ser Ser Lys Arg Ser Gln Gln His Ala Lys Val Val
        115                 120                 125

Pro Trp Met Arg Lys Thr Glu Tyr Ile Ser Thr Glu Phe Asn Arg Tyr
    130                 135                 140

Gly Ile Ser Asn Glu Lys Pro Glu Val Lys Ile Gly Val Ser Val Lys
145                 150                 155                 160

Gln Gln Phe Thr Glu Glu Ile Tyr Lys Asp Arg Asp Ser Gln Ile
                165                 170                 175

Thr Ala Ile Glu Lys Thr Phe Glu Asp Ala Gln Lys Ser Ile Ser Gln
            180                 185                 190

His Tyr Ser Lys Pro Arg Val Thr Pro Val Glu Val Met Pro Val Phe
        195                 200                 205

Pro Asp Phe Lys Met Trp Ile Asn Pro Cys Ala Gln Val Ile Phe Asp
    210                 215                 220

Ser Asp Pro Ala Pro Lys Asp Thr Ser Gly Ala Ala Ala Leu Glu Met
```

-continued

```
                225                 230                 235                 240
        Met Ser Gln Ala Met Ile Arg Gly Met Met Asp Glu Glu Gly Asn Gln
                        245                 250                 255

Phe Val Ala Tyr Phe Leu Pro Val Glu Glu Thr Leu Lys Lys Arg Lys
                    260                 265                 270

Arg Asp Gln Glu Glu Met Asp Tyr Ala Pro Asp Asp Val Tyr Asp
                275                 280                 285

Tyr Lys Ile Ala Arg Glu Tyr Asn Trp Asn Val Lys Asn Lys Ala Ser
            290                 295                 300

Lys Gly Tyr Glu Glu Asn Tyr Phe Phe Ile Phe Arg Glu Gly Asp Gly
        305                 310                 315                 320

Val Tyr Tyr Asn Glu Leu Glu Thr Arg Val Arg Leu Ser Lys Arg Arg
                        325                 330                 335

Ala Lys Ala Gly Val Gln Ser Gly Thr Asn Ala Leu Leu Val Val Lys
                    340                 345                 350

His Arg Asp Met Asn Glu Lys Glu Leu Glu Ala Gln Glu Ala Arg Lys
                355                 360                 365

Ala Gln Leu Glu Asn His Glu Pro Glu Glu Glu Glu Glu Glu Glu Met
            370                 375                 380

Glu Thr Glu Glu Lys Glu Ala Gly Gly Ser Asp Glu Glu Gln Glu Lys
        385                 390                 395                 400

Gly Ser Ser Ser Glu Lys Gly Ser Glu Asp Glu His Ser Gly Ser
                        405                 410                 415

Glu Ser Glu Arg Glu Gly Asp Arg Asp Glu Ala Ser Asp Lys Ser
                    420                 425                 430

Gly Ser Gly Glu Asp Glu Ser Ser Glu Asp Glu Ala Arg Ala Ala Arg
                435                 440                 445

Asp Lys Glu Glu Ile Phe Gly Ser Asp Ala Asp Ser Glu Asp Ala
            450                 455                 460

Asp Ser Asp Asp Glu Asp Arg Gly Gln Ala Gln Gly Ser Asp Asn
        465                 470                 475                 480

Asp Ser Asp Ser Gly Ser Asn Gly Gly Gly Gln Arg Ser Arg Ser His
                        485                 490                 495

Ser Arg Ser Ala Ser Pro Phe Pro Ser Gly Ser Glu His Ser Ala Gln
                    500                 505                 510

Glu Asp Gly Ser Glu Ala Ala Ala Ser Asp Ser Ser Glu Ala Asp Ser
                515                 520                 525

Asp Ser Asp
            530

<210> SEQ ID NO 3
<211> LENGTH: 20
<212> TYPE: DNA
<213> ORGANISM: Homo sapiens

<400> SEQUENCE: 3
agtgacaaga gtggcagtgg                                                    20

<210> SEQ ID NO 4
<211> LENGTH: 20
<212> TYPE: DNA
<213> ORGANISM: Homo sapiens

<400> SEQUENCE: 4
gaggacagag gacaggccca                                                    20
```

-continued

```
<210> SEQ ID NO 5
<211> LENGTH: 20
<212> TYPE: DNA
<213> ORGANISM: Homo sapiens

<400> SEQUENCE: 5
cactcggccc aggaggatgg                                               20

<210> SEQ ID NO 6
<211> LENGTH: 20
<212> TYPE: DNA
<213> ORGANISM: Homo sapiens

<400> SEQUENCE: 6
gacagtgact gagtcccagg                                               20

<210> SEQ ID NO 7
<211> LENGTH: 19
<212> TYPE: DNA
<213> ORGANISM: Homo sapiens

<400> SEQUENCE: 7
ctggatggtg ggcgccata                                                19

<210> SEQ ID NO 8
<211> LENGTH: 19
<212> TYPE: DNA
<213> ORGANISM: Homo sapiens

<400> SEQUENCE: 8
cctggtcccg ctttcgttt                                                19

<210> SEQ ID NO 9
<211> LENGTH: 19
<212> TYPE: DNA
<213> ORGANISM: Homo sapiens

<400> SEQUENCE: 9
ctaaggcgga ccctggttt                                                19

<210> SEQ ID NO 10
<211> LENGTH: 21
<212> TYPE: PRT
<213> ORGANISM: Homo sapiens

<400> SEQUENCE: 10

Arg Tyr Gly Ile Ser Asn Glu Lys Pro Glu Val Lys Ile Gly Val Ser
 1               5                  10                  15

Val Lys Gln Gln Phe
            20

<210> SEQ ID NO 11
<211> LENGTH: 22
<212> TYPE: PRT
<213> ORGANISM: Homo sapiens

<400> SEQUENCE: 11

Glu Thr Arg Val Arg Leu Ser Lys Arg Arg Ala Lys Ala Gly Val Gln
 1               5                  10                  15

Ser Gly Thr Asn Ala Leu
            20
```

```
<210> SEQ ID NO 12
<211> LENGTH: 18
<212> TYPE: DNA
<213> ORGANISM: Homo sapiens

<400> SEQUENCE: 12
ttcagtcagg caccaacg                                              18

<210> SEQ ID NO 13
<211> LENGTH: 18
<212> TYPE: DNA
<213> ORGANISM: Homo sapiens

<400> SEQUENCE: 13
cgctggccac ccccattg                                              18

<210> SEQ ID NO 14
<211> LENGTH: 11
<212> TYPE: PRT
<213> ORGANISM: Homo sapiens

<400> SEQUENCE: 14

Arg Val Arg Leu Ser Lys Arg Arg Ala Lys Ala
 1               5                  10

<210> SEQ ID NO 15
<211> LENGTH: 39
<212> TYPE: PRT
<213> ORGANISM: Drosophila melanogaster

<400> SEQUENCE: 15

Ser Asp Arg Arg Ser Asn Lys Pro Ile Met Glu Lys Arg Arg Arg Ala
 1               5                  10                  15

Arg Ile Asn Asn Cys Leu Asn Glu Leu Lys Ala Asp Ile Leu Glu Lys
                20                  25                  30

Thr Val Lys His Leu Gln Glu
         35

<210> SEQ ID NO 16
<211> LENGTH: 40
<212> TYPE: PRT
<213> ORGANISM: Homo sapiens

<400> SEQUENCE: 16

His Arg Pro Asn Ser His Arg Thr Leu Pro Glu Arg Ser Val Val Cys
 1               5                  10                  15

Arg Val Lys Tyr Cys Asn Ser Leu Asp Ala Thr Ser Leu Glu Lys Gln
                20                  25                  30

His Lys His Asp Leu Leu Thr Glu
         35                  40

<210> SEQ ID NO 17
<211> LENGTH: 18
<212> TYPE: PRT
<213> ORGANISM: Homo sapiens

<400> SEQUENCE: 17

Ser Phe Gly Glu Leu Ala Leu Ile Tyr Gly Tyr Pro Arg Ala Ala Thr
 1               5                  10                  15

Val Lys

<210> SEQ ID NO 18
```

-continued

```
<211> LENGTH: 18
<212> TYPE: PRT
<213> ORGANISM: Homo sapiens

<400> SEQUENCE: 18

Tyr Phe Gly Glu Ile Ala Leu Leu Leu Asn Arg Pro Arg Ala Ala Thr
1               5                   10                  15

Val Val

<210> SEQ ID NO 19
<211> LENGTH: 20
<212> TYPE: PRT
<213> ORGANISM: Escherichia coli

<400> SEQUENCE: 19

Phe Ile Gly Glu Leu Gly Leu Phe Glu Gly Gln Glu Arg Ser Arg Ala
1               5                   10                  15

Lys Thr Ala Cys
            20

<210> SEQ ID NO 20
<211> LENGTH: 20
<212> TYPE: PRT
<213> ORGANISM: Homo sapiens

<400> SEQUENCE: 20

Tyr Tyr Asn Glu Leu Glu Thr Arg Val Arg Leu Ser Lys Arg Arg Ala
1               5                   10                  15

Lys Ala Gly Val
            20

<210> SEQ ID NO 21
<211> LENGTH: 13
<212> TYPE: PRT
<213> ORGANISM: Homo sapiens

<400> SEQUENCE: 21

Asp Tyr Lys Asp Asp Asp Gly Ser Lys Ser Ala Ile Phe
1               5                   10

<210> SEQ ID NO 22
<211> LENGTH: 4
<212> TYPE: PRT
<213> ORGANISM: Homo sapiens

<400> SEQUENCE: 22

Lys Lys Arg Lys
1
```

ANTIBODIES IMMUNOLOGICALLY SPECIFIC FOR PD2, A PROTEIN THAT IS AMPLIFIED AND OVEREXPRESSED IN PANCREATIC CANCER

This application is a Divisional of U.S. patent application Ser. No. 09/647,143, filed Sep. 27, 2000 now U.S. Pat. No. 6,680,196 which is a §371 application of PCT/US99/06633, filed Mar. 26, 1999 which in turn claims priority under 35 U.S.C. §119(e) to US Provisional Application No. 60/079,649 filed Mar. 27, 1998. The entire disclosures of each of the above-identified applications is incorporated by reference herein.

Pursuant to 35 U.S.C. §202(c) it is acknowledged that the U.S. Government has certain rights in the invention described herein, which was made in part with funds from the National Institutes of Health, Grant Numbers: RO1 DK 46589, RO1 CA 47507, P30 CA 36727 and P50CA72712-01.

FIELD OF THE INVENTION

This invention relates to the fields of molecular biology and neoplastic disease, and more specifically, to isolated nucleic acids, proteins, antibodies, methods and kits containing the same which are useful in genetic screening assays, and in the design of clinically beneficial chemotherapeutic agents which inhibit the aberrant cellular proliferation in tumor cells.

BACKGROUND OF THE INVENTION

Several publications are referenced in this application by author name and year of publication in parentheses in order to more fully describe the state of the art to which this invention pertains. The disclosure of each of these publications is incorporated by reference herein.

Pancreatic cancer is the fifth leading cause of death by cancer in the United States. Twenty-four thousand people die each year from this disease. The 5-year survival for pancreatic cancer patients is less than 5% and the incidence of the disease has tripled over the last 40 years. The molecular basis underlying the pathogenesis of pancreatic adenocarcinoma remains unknown. As a result, the disease has an extremely poor prognosis and lacks early diagnostic and therapeutic modalities.

Normal cellular proliferation is finely regulated by the expression of growth-promoting proto-oncogenes and growth-controlling anti-oncogenes. Mutations, rearrangements, deletions, or amplifications that potentiate the activities of proto-oncogenes result in tumor formation. Similar events that inactivate anti-oncogenes or tumor suppressor genes disrupt their role in the cell as negative regulators of cell growth and proliferation.

Gene amplification has been implicated as a common mechanism by which tumor cells acquire a chemotherapy resistant phenotype. Some amplification units arise at the site of the normal gene, but disperse into the cytoplasm as double minutes (DMs). These DMs may become reincorporated and reamplified as homogeneously staining regions (HSRs) or abnormal banding regions (ABRs) at other sites in the genome. DMs and HSRs may be alternate forms of amplified DNA. The DMs are not inherited stably during cell division because of the lack of centromeres. Integration of DMs into a chromosome is thought to result in the formation of HSRs, which represent a more stable, form of the amplified DNA which is maintained as the cell divides. The mechanisms underlying this process are not completely understood, but appear to be based on recombination and unequal distribution of the amplified DNA into daughter cells.

Cytogenetic amplification has been observed in 8 of 63 primary pancreatic adenocarcinomas analyzed for the presence of DMs. The expression of epidermal growth factor, epidermal growth factor receptor, transforming growth factor, erbB-2, erbB-3, and c-met are elevated in pancreatic cancer (Barton et al., 1991; Korc et al., 1992; Lemoine et al., 1992; Prat et al., 1991).

Using restriction landmark genomic scanning (RLGS), Miwa et al (1996) identified a locus at chromosome 19q13.1-q13.2 including the AKT2 gene which was amplified in 20% of pancreatic cancer. Over expression of the AKT2 gene was further shown to be associated with the malignant phenotype of a subset of human ductal pancreatic cancers (Cheng et al., 1996).

No well-defined differentiation pathway has been shown in pancreatic adenocarcinomas, and the biology of this tumor type is generally poorly understood. The present inventors have appreciated a need for the isolation of essential components involved in the regulation of differentiation and proliferation of pancreatic tumor cells. Molecular elucidation of these components will provide novel targets for the development of antiproliferative and diagnostic agents for cancer treatment and diagnosis.

SUMMARY OF THE INVENTION

This invention provides novel, biological molecules useful for identification, detection, and/or molecular characterization of components involved in the regulation of cellular differentiation and tumorigenesis. According to one aspect of the invention, an isolated nucleic acid molecule is provided which includes an isolated open reading frame encoding a phosphoprotein of a size between about 60 to 70 kilodaltons. The encoded protein, referred to herein as PD2, comprises a tripartite domain structure including a nuclear transport signal, a helix-loop-helix domain, a nucleotide binding site, and several putative phosphorylation sites.

In a preferred embodiment of the invention, an isolated nucleic acid molecule is provided that includes a DNA encoding a human PD2 protein. In a particularly preferred embodiment, the human PD2 protein has an amino acid sequence the same as SEQ ID NO:2. An exemplary PD2 nucleic acid molecule of the invention comprises SEQ ID NO:1.

According to another aspect of the present invention, an isolated nucleic acid molecule is provided, which has a sequence selected from the group consisting of: (1) SEQ ID NO:1; (2) a sequence specifically hybridizing with preselected portions or all of the complementary strand of SEQ ID NO:1; (3) a sequence comprising preselected portions of SEQ ID NO:1, (4) a sequence encoding part or all of a polypeptide having amino acid SEQ ID NO:2. Such partial sequences are useful as probes to identify and isolate homologues of the PD2 gene of the invention. Accordingly, isolated nucleic acid sequences encoding natural allelic variants of the nucleic acids of SEQ ID NO:1 are also contemplated to be within the scope of the present invention. The term natural allelic variants will be defined hereinbelow.

According to another aspect of the present invention, isolated human PD2 protein is provided. PD2 is a phosphoprotein with a deduced molecular weight of between about 60 kDa and 70 kDa. PD2 comprises a tripartite domain structure including a nuclear transport signal, a helix-loophelix domain, a cyclic AMP or related nucleotide binding site, and several putative phosphorylation sites. The expression of this PD2 protein correlates with the deregulated growth of highly undifferentiated pancreatic adenocarcinomas.

In a preferred embodiment of the invention, the protein is of human origin, and has the amino acid sequence of SEQ ID NO:2. In a further embodiment the protein may be encoded by natural allelic variants of SEQ ID NO:1. Inasmuch as certain amino acid variations may be present in human PD2 protein encoded by natural allelic variants, such proteins are also contemplated to be within the scope of the invention.

According to another aspect of the present invention, antibodies immunologically specific for the human PD2 protein described hereinabove are provided.

Host cells comprising the PD2 encoding nucleic acids of the invention are also contemplated to be within the scope of the present invention. Such host cells include but are not limited to bacterial cells, mammalian cells, insect cells, fungal cells, and plant cells. The PD2-encoding nucleic acids may be conveniently cloned into a plasmid or retroviral vector for introduction into host cells. Such cells are useful in screening methods to identify compounds which regulate and/or inhibit PD2 expression. Compounds so identified may have therapeutic value in the treatment of pancreatic cancer.

The present invention also encompasses transgenic mice expressing the PD2 encoding nucleic acids of the invention. The PD2 encoding DNA may be altered to include any of the following, mutations, alterations, deletions, insertions. In another embodiment, PD2 knockout mice may be generated to assess the contribution of the PD2 gene to growth and development.

This invention also provides methods for genetic screening and diagnostic evaluation of patients at risk for, or currently suffering from, cancer of the pancreas. The hybridization specificity of the nucleic acids of the invention may be used for differential evaluation of patients presenting with phenotypic characteristics common to pancreatic cancer. The nucleic acid molecules of the invention can be used as diagnostic hybridization probes or as primers for diagnostic PCR analysis for PD2 or mutations thereof. Additionally, antisense molecules which may be useful in the regulation of PD2 expression are provided herein. Other methods encompassed by the present invention include immunodetection methods for assessing biological samples for the presence of PD2 proteins.

In another aspect of the present invention, kits are provided for practicing the methods set forth above. An exemplary kit for screening tumor samples for PD2 expression includes for example, suitable primers for PCR amplification of target PD2 sequences. Exemplary primers include those having the sequence of SEQ ID NOS: 12 and 13. A kit in accordance with the invention may also contain vials, buffers, a target PD2 sequence as a positive control and a protocol sheet. Another exemplary kit may employ immunological methodology. Kits of this type include immobilized PD2 protein and antibodies immunologically specific for PD2. Such kits may be used in for immunological assessment of biopsy specimens for identification and/or quantification of PD2 in pancreatic tissues.

The term "isolated nucleic acid" is sometimes used with reference to nucleic acids of the invention. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the genomic DNA of a prokaryote or eukaryote.

When used with reference to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a substantially pure form.

The terms "isolated protein" or "isolated and purified protein" are sometimes used herein to refer to a protein produced by expression of an isolated nucleic acid molecule of the invention. Alternatively, these terms may refer to a protein which has been sufficiently separated from other proteins with which it would naturally be associated, so as to exist in substantially pure form.

The term "substantially pure" refers to a preparation comprising at least 50–60% by weight of the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., PD2), but which do not substantially recognize and bind other molecules in a sample containing a mixed population of antigenic biological molecules.

With respect to nucleic acids and oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). When used in reference to a double stranded nucleic acid, this term is intended to signify that the double stranded nucleic acid has been subjected to denaturing conditions, as is well known to those of skill in the art. In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The nucleic acids, proteins, and antibodies, of the present invention may be used to advantage diagnostic reagents and tools for assessing the malignant potential of pancreatic adenocarcinomas. They may also be used as targets for the development of novel chemotherapeutic agents that regulate differentiation and/or inhibit aberrant cellular proliferation in tumor cells. The transgenic mice of the invention provide a means to assess the function of PD2 in vivo.

The human PD2 molecules described are above may also be used as research tools and will facilitate the elucidation of the genetic and protein interactions involved in the regulation of cell division, differentiation, and neoplastic transformation. Methods and kits employing such molecules are also provided.

BRIEF DESCRIPTION OF THE DRAWINGS

FIG. 1A shows the hybridization of a $^{32}$P-labelled PD2 cDNA probe. PD2 is expressed at 30-fold higher levels in Panc 1 cells as compared to HPAF/CD-11 cells. FIG. 1B shows an autoradiogram of the same blot hybridized with a $^{32}$P-labelled β-actin probe confirming equivalent loading of RNA per lane.

FIG. 2 depicts the nucleotide (SEQ ID NO:1) and deduced amino acid (SEQ ID NO:2) sequence of PD2 cDNA. The nucleotide sequence is numbered in the left-hand margin. The deduced amino acid sequence is numbered in the right-hand margin. The polyadenylation signal is underlined.

FIG. 4A reveals the relative positions of three putative protein motifs: a helix-loop-helix domain, a nuclear localization domain, and an Arg-rich RNA binding/cAMP binding domain, indicated by boxes. FIG. 4B uses boxes to depict the regions of sequence identity between various proteins (listed in Table 1) and the deduced amino acid sequence of PD2 protein.

FIG. 5 shows the alignment of the helix-loop-helix domain of the deduced PD2 amino acid sequence with the helix-loop-helix domain of the *Drosophila* Hairy protein (20). The top sequence labeled "A." represents amino acid residues 30–87 of the *Drosophila* Hairy protein, and the bottom sequence labled "B." represents amino acid residues 15–77 of the PD2 protein. Note that the amino acid residues within the "loop" regions are not directly shown or listed in the alignment. Boxed residues indicate identity between the two sequences. Asterisks. (*) indicate identity in the PD2 sequence with other members of the helix-loop-helix family of proteins (35).

FIG. 6 shows an alignment of PD2 residues with consensus cAMP binding domains of the bacterial catabolite activator protein, and the regulatory subunit of the eukaryotic cAMP-dependent protein kinase. Row A shows residues 198–213 of the RIβ isoform of the regulatory type I subunit of cAMP dependent protein kinase (16). Row B shows residues 322–337 of the RIβ isoform of the regulatory type I subunit of cAMP dependent protein kinase (16). Row C shows residues 69–88 of the *E. coli* catabolite gene activator protein (16). Row D shows residues 322–341 of the deduced PD2 sequence (FIG. 2). Identity among the amino acid sequences is indicated with boxes around the identical residues.

FIG. 8A shows the results obtained following hybridization with a $^{32}$P_labelled PD2 cDNA probe. FIG. 8B shows hybridization results obtained using a $^{32}$P-labelled 1-actin cDNA probe confirming equivalent loading of RNA per lane.

FIG. 9A shows hybridization results obtained using a $^{32}$P-labelled PD2 cDNA probe. FIG. 9B depicts the results obtained using a $^{32}$P_labelled β-actin cDNA probe, to confirm equivalent loading of RNA per lane.

DETAILED DESCRIPTION OF THE INVENTION

Figure 1A:
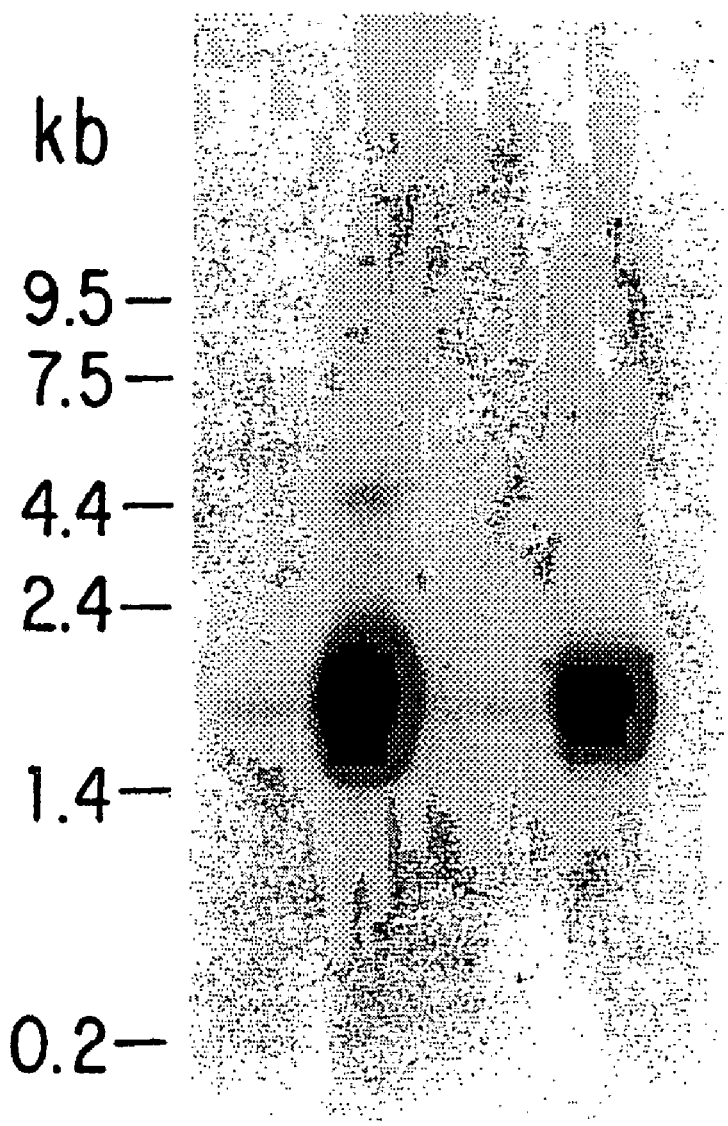
FIGS. 1A and 1B show autoradiographs of Northern blot analysis of RNA isolated from differentiated and undifferentiated pancreatic cell lines. Total RNA (20 μg; lanes 1 and 2) or poly(A+) RNA (lanes 3 and 4) was separated by gel electrophoresis and transferred to a nitrocellulose membrane. Lanes 1 and 3 contained RNA from the differentiated pancreatic cell line HPAF/CD-11. Lanes 2 and 4 contained RNA from the highly undifferentiated pancreatic cell line Panc 1.

Adenocarcinomas of the pancreatic ducts make up over 95% of pancreatic nonendocrine tumors, although the duct system accounts for a minor proportion of the normal gland. Accurate staging of pancreatic cancer is required to evaluate treatment modalities such as surgical resection, radiotherapy and chemotherapy. A universally satisfactory staging system has not been devised, although several staging systems have been introduced for clinical practice (reviewed in Eskelinen and Lipponen, 1992). The grading of pancreatic adenocarcinomas utilizes generally accepted principles of glandular differentiation, nuclear size and mitotic activity (Kloppel et al., 1985), but subjectivity in assessment and heterogeneity are common. Accurate histological classification of these tumors accordingly, has prognostic relevance and should aid in the selection of appropriate therapy.

Well-differentiated tumors (grade 1) contain duct like structures with polarized cells. Moderately differentiated tumors (grade 2) contain less differentiated duct-like and tubular glands. Poorly differentiated tumors (grade 3) contain pleomorphic structures, poorly-differentiated glands, minimal mucus production and large nuclei. The most differentiated tumors grow as tubular structures with a common luminal space, while less differentiated tumors show a loss of cell polarity resulting in secretion into both luminal and interstitial space (Kern et al., 1987). The tumor growth rate of poorly-differentiated tumors is twice that for well differentiated tumors. Median survival times are correlated with the tumor grade: patients with poorly-differentiated tumors survived for a shorter time than did patients with well-differentiated tumors (Kloppel et al., 1985; Eskelinen and Lipponen, 1992).

In an effort to identify differentially expressed or overexpressed genes that play a role in maintaining distinct morphological differentiation features exhibited by pancreatic adenocarcinoma cells, a cDNA library from a poorly differentiated human pancreatic tumor cell line, Panc 1 (1,2), was screened with single stranded cDNA probes generated from mRNA prepared from Panc 1 and a well-differentiated human pancreatic tumor cell line, HPAF/CD11 (3). One cDNA clone (PD-2) detected an mRNA expressed at levels 30-fold higher in Panc 1 cells, as compared to HPAF/CD-11 cells. A similar amplification was observed in the gene copy number by Southern analysis. The present invention provides the nucleotide sequence, deduced amino acid sequence, and chromosomal location of this previously undescribed cDNA. The availability of these sequences enables the practice of genetic screening assays for classifying particular pancreatic tumors as well as providing novel targets for the development of clinically relevant chemotherapeutic agents.

I. Preparation of Human PD2-Encoding Nucleic Acid Molecules, PD2 Proteins, and Antibodies Thereto A. Nucleic Acid Molecules Nucleic acid molecules encoding the human PD2 proteins of the invention may be prepared by two general methods: (1) synthesis from appropriate nucleotide triphosphates, or (2) isolation from biological sources. Both methods utilize protocols well known in the art. The availability of nucleotide sequence information, such as a cDNA having the sequence of SEQ ID NO:1 enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.9 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.9 kb double-stranded molecule. A synthetic DNA molecule so constructed may then be cloned and amplified in an appropriate vector.

Nucleic acid sequences encoding the human PD2 protein may be isolated from appropriate biological sources using methods known in the art. In a preferred embodiment, a cDNA clone is isolated from a cDNA expression library of human origin. In an alternative embodiment, utilizing the sequence information provided by the cDNA sequence, human genomic clones encoding PD2 proteins may be isolated. Suitable probes for this purpose are derived from sequences within the PD2 cDNA and include the following sequences:

```
5' AGTGACAAGAGTGGCAGTGG 3'      (SEQ ID NO: 3)

5' GAGGACAGAGGACAGGCCCA 3'      (SEQ ID NO: 4)

5' CACTCGGCCCAGGAGGATGG 3'      (SEQ ID NO: 5)

5' GACAGTGACTGAGTCCCAGG 3'      (SEQ ID NO: 6)
```

Such probes may be between 15 and 40 nucleotides in length. For probes longer than those shown above, the additional contiguous nucleotides are provided within SEQ ID NO:1.

Additionally, cDNA or genomic clones having homology with human PD2 may be isolated from other species using oligonucleotide probes corresponding to predetermined sequences within the human PD2 encoding nucleic acids.

In accordance with the present invention, nucleic acids having the appropriate level of sequence homology with the protein coding region of SEQ ID NO:1 may be identified by using hybridization and washing conditions of appropriate stringency. For example, hybridizations may be performed, according to the method of Sambrook et al., *Molecular Cloning*, Cold Spring Harbor Laboratory (1989), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology (Sambrook et al., 1989) is as follows:

$$T_m = 81.5° C. + 16.6 \text{ Log } [Na+] + 0.41(\% G+C) - 0.63$$
$$(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell.

PD2-encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention, such as selected segments of the cDNA having SEQ ID NO:1. As mentioned previously, such oligonucleotides are useful as probes for detecting or isolating PD2 genes.

Antisense nucleic acid molecules may be targeted to translation initiation sites and/or splice sites to inhibit the expression of the PD2 gene or production of the PD2 protein of the invention. Such antisense molecules are typically between 15 and 30 nucleotides in length and often span the translational start site of PD2 encoding mRNA molecules. Suitable antisense molecules for controlling the expression of PD2 are as follows:

```
5' CTGGATGGTGGGCGCCATA 3'       (SEQ ID NO: 7)

5' CCTGGTCCCGCTTTCGTTT 3'       (SEQ ID NO: 8)

5' CTAAGGCGGACCCTGGTTT 3'       (SEQ ID NO: 9)
```

Alternatively, antisense constructs may be generated which contain the entire PD2 cDNA in reverse orientation. Such antisense constructs are exemplified herein.

It will be appreciated by persons skilled in the art that variants (e.g., allelic variants) of PD2 sequences exist in the human population, and must be taken into account when designing and/or utilizing oligonucleotides of the invention. Accordingly, it is within the scope of the present invention to encompass such variants, with respect to the PD2 sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants. Additionally, the term "substantially complementary" refers to oligonucleotide sequences that may not be perfectly matched to a target sequence, but such mismatches do not materially affect the ability of the oligonucleotide to hybridize with its target sequence under the conditions described.

B. Proteins

Full-length human PD2 protein of the present invention may be prepared in a variety of ways, according to known methods. The protein may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding PD2 protein enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or Gibco-BRL, Gaithersburg, Md.

Alternatively, according to a preferred embodiment, larger quantities of PD2 protein may be produced by expression in a suitable prokaryotic or eukaryotic system. For example, part or all of a DNA molecule, such as a cDNA having SEQ ID NO:1 may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

The human PD2 protein produced by gene expression in a recombinant procaryotic or eukaryotic system may be purified according to methods known in the art. In a preferred embodiment, a commercially available expression/ secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Alternative tags may comprise the FLAG epitope or the hemagglutinin epitope. Such methods are commonly used by skilled practitioners.

The human PD2 protein of the invention, prepared by the aforementioned methods, may be analyzed according to standard procedures. For example, such protein may be subjected to amino acid sequence analysis, according to known methods.

The present invention also provides antibodies capable of immunospecifically binding to proteins of the invention. Polyclonal antibodies directed toward human PD2 protein may be prepared according to standard methods. In a preferred embodiment, monoclonal antibodies are prepared, which react immunospecifically with the various epitopes of the PD2 protein described herein. Monoclonal antibodies may be prepared according to general methods of Köhler and Milstein, following standard protocols. Polyclonal or monoclonal antibodies that immunospecifically interact with PD2 protein can be utilized for identifying and purifying such protein. For example, antibodies may be utilized for affinity separation of proteins with which they immunospecifically interact. Antibodies may also be used to immunoprecipitate proteins from a sample containing a mixture of proteins and other biological molecules. Other uses of anti-PD2 antibodies are described below.

II. Uses of PD2-Encoding Nucleic Acids, PD2 Proteins and Antibodies Thereto

Cellular signalling molecules have received a great deal of attention as potential prognostic indicators of neoplastic disease and as therapeutic agents to be used for a variety of purposes in cancer chemotherapy. The PD2 protein of the invention is intimately involved in the regulation of differentiation and neoplastic growth. The biochemical and molecular interactions of the PD2 gene and protein involved in the genesis and maintenance of the transformed state and in the maintenance of an undifferentiated state provide novel targets for the development of chemotherapeutic reagents that may be used to block the growth of tumor cells and/or promote differentiation.

Additionally, PD2 nucleic acids, proteins and antibodies thereto, according to this invention, may be used as research tools to identify other proteins that are involved in differentiation and transformation processes.

A. PD2-Encoding Nucleic Acids

PD2-encoding nucleic acids may be used for a variety of purposes in accordance with the present invention. PD2-encoding DNA, RNA, or fragments thereof may be used as probes to detect the presence of and/or expression of genes encoding PD2 proteins. Methods in which PD2-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The PD2-encoding nucleic acids of the invention may also be utilized as probes to identify related genes from other animal species. As is well known in the art, hybridization stringencies may be adjusted to allow hybridization of nucleic acid probes with complementary sequences of varying degrees of homology.

Thus, PD2-encoding nucleic acids may be used to advantage to identify and characterize other genes of varying degrees of relation to the PD2 genes of the invention thereby enabling further characterization of the aberrant cell growth associated with pancreatic adenocarcinomas. Additionally, the nucleic acids of the invention may be used to identify genes encoding proteins that interact with PD2 proteins (e.g., by the "interaction trap" technique), which should further accelerate identification of the components involved in regulation of cellular proliferation.

Nucleic acid molecules, or fragments thereof, encoding PD2 genes may also be utilized to control the production of PD2 proteins, thereby regulating the amount of protein available to participate in the maintenance of deregulated cell growth. As mentioned above, antisense oligonucleotides corresponding to essential processing sites in PD2-encoding mRNA molecules may be utilized to inhibit PD2 protein production in targeted cells. Alterations in the physiological amount of PD2 proteins may dramatically affect the activity of other protein factors involved in the regulation of cell division.

The PD2 nucleic acids of the invention may be introduced into host cells. In a preferred embodiment, mammalian cell lines are provided with comprise a PD2-encoding nucleic acid or a variant thereof. Host cells contemplated for use include, but are not limited to NIH3T3, CHO, HELA, yeast, bacteria, insect and plant cells. The PD2 encoding nucleic acids may be operably linked to appropriate regulatory expression elements suitable for the particular host cell to be utilized. Methods for introducing nucleic acids into host cells are well known in the art. Such methods include, but are not limited to, transfection, transformation, calcium phosphate precipitation, electroporation and lipofection.

The host cells described above may be used as screening tools to identify compounds which modulate PD2 activity. Modulation of PD2 activity may be assessed by measuring alterations in PD2 phosphorylation in the presence of the test compound. The morphology of PD2 expressing cells may also be altered in the presence of the test compound. Finally, test compounds will be assessed for the induction of certain pancreatic differentiation markers, such as MUC-1 and carbonic anhydrase.

The availability of PD2 encoding nucleic acids enables the production of strains of laboratory mice carrying part or all of the PD2 gene or mutated sequences thereof, in single or amplified copies. Such mice may provide an in vivo model for cancer, and may be particularly useful in studying pancreatic cancer. Alternatively, the human PD2 nucleic acid sequence information provided herein enables the cloning of the murine homolog for use in the production of knockout mice in which the endogenous gene encoding PD2 has been specifically inactivated. Methods of introducing transgenes and knockouts in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic and knockout mice described above will facilitate the molecular elucidation of the role PD2 proteins play in differentiation and tumorigenesis.

The alterations to the PD2 gene envisioned herein include modifications, deletions, and substitutions. Modifications and deletions render the naturally occurring gene nonfunctional, producing a "knock out" animal. Substitutions of the naturally occurring gene for a gene from a second species results in an animal which produces an PD2 gene from the second species. Substitution of the naturally occurring gene for a gene having a mutation results in an animal with a mutated PD2 protein. A transgenic mouse carrying the human PD2 gene is generated by direct replacement of the mouse PD2 gene with the human gene. These transgenic animals are valuable for use in vivo assays for elucidation of other medical disorders associated with cellular activities modulated by PD2 genes. A transgenic animal carrying a "knock out" of a PD2 encoding nucleic acid is useful for the establishment of a nonhuman model for pancreatic cancer involving PD2 regulation.

As a means to define the role that PD2 plays in mammalian systems, mice can be generated that cannot make PD2 proteins because of a targeted mutational disruption of a PD2 gene.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered PD2 gene generally should not fully encode the same PD2 protein native to the host animal and its expression product should be altered to a minor or great degree, or absent altogether. However, it is conceivable that a more modestly modified PD2 gene will fall within the compass of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated PD2 genes to selectively inactivate the wild-type gene in totipotent ES cells (such as those described above) and then generate transgenic mice. The use of gene-targeted ES cells in the generation of gene-targeted transgenic mice is known in the art.

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Knockout mice of the invention can be injected with tumor cells or treated with carcinogens to generate carcinomas. Such mice provide a biological system for assessing the role played by a PD2 gene of the invention. Accordingly, therapeutic agents which inhibit the action of PD2 proteins may be screened in studies using PD2 knock out mice.

As described above, PD2-encoding nucleic acids are also used to advantage to produce large quantities of substantially pure PD2 proteins, or selected portions thereof.

B. PD2 Protein and Antibodies

Purified PD2 protein, or fragments thereof, may be used to produce polyclonal or monoclonal antibodies which also may serve as sensitive detection reagents for the presence and accumulation of PD2 protein (or complexes containing PD2 protein) in mammalian cells. Recombinant techniques enable expression of fusion proteins containing part or all of PD2 protein. The full length protein or fragments of the protein may be used to advantage to generate an array of monoclonal antibodies specific for various epitopes of PD2 protein, thereby providing even greater sensitivity for detection of PD2 protein in cells.

Polyclonal or monoclonal antibodies immunologically specific for PD2 protein may be used in a variety of assays designed to detect and quantitate the protein. Such assays include, but are not limited to: (1) flow cytometric analysis; (2) immunochemical detection/localization of PD2 protein in tumor cells or cells in various stages of differentiation; and (3) immunoblot analysis (e.g., dot blot, Western blot) of extracts from various cells. Additionally, as described above, anti-PD2 antibodies can be used for purification of PD2 protein and any associated subunits (e.g., affinity column purification, immunoprecipitation).

From the foregoing discussion, it can be seen that PD2-encoding nucleic acids, PD2 expressing vectors, PD2 protein and anti-PD2 antibodies of the invention can be used to detect PD2 gene expression and alter PD2 protein accumulation for purposes of assessing the genetic and protein interactions involved in the control of differentiation and transformation pathways.

C. Methods of use for the Compositions of the Invention and Kits for Preforming the Disclosed Methods.

From the foregoing discussion, it can be seen that PD2-encoding nucleic acids, PD2-expressing vectors, PD2 proteins and anti-PD2 antibodies of the invention can be used to detect PD2 gene expression and alter PD2 protein accumulation for purposes of assessing the genetic and protein interactions involved in malignant transformation of pancreatic cells.

Exemplary approaches for detecting PD2 nucleic acid or polypeptides/proteins include:

a) comparing the sequence of nucleic acid in the sample with the PD2 nucleic acid sequence to determine whether the sample from the patient contains mutations; or b) determining the presence, in a sample from a patient, of the polypeptide encoded by the PD2 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal PD2 gene or from known mutations thereof; or, d) using a specific binding member capable of binding to a PD2 nucleic acid sequence (either normal sequence or known mutated sequence), the specific binding member comprising nucleic acid hybridizable with the PD2 sequence, or substances comprising an antibody domain with specificity for a native or mutated PD2 nucleic acid sequence or the polypeptide encoded by it, the specific binding member being labelled so that binding of the specific binding member to its binding partner is detectable; or, e) using PCR involving one or more primers based on normal or mutated PD2 gene sequence to screen for normal or mutant PD2 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for cancer susceptibility alleles, the PD2 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the PD2 gene and its association with cancer paves the way for aspects of the present invention to provide the use of materials and methods, such as are disclosed and discussed above, for establishing the presence or absence in a test sample of a variant form of the gene, in particular an allele or variant specifically associated with cancer, especially pancreatic cancer. This may be for diagnosing a predisposition of an individual to cancer. It may be for diagnosing cancer of a patient with the disease as being associated with the gene.

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides.

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a PD2 gene encoded protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing the PD2 antigen, such as a pancreas or lymph node tissue section or specimen, a homogenized tissue extract, an isolated cell, a cell membrane preparation, separated or purified forms of any of the above protein-containing compositions, or even any biological fluid that comes into contact with pancreatic tissues, including blood and lymphatic fluid.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The immunodetection methods of the present invention have evident utility in the diagnosis of pancreatic cancer. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients with pancreatic cancer, the detection of PD2 antigen, or an increase in the levels of such an antigen, in comparison to the levels in a corresponding biological sample from a normal subject is indicative of a patient with pancreatic cancer. The basis for such diagnostic methods lies, in part, with the finding that the PD2 nucleic acid identified in the present invention is overexpressed in pancreatic cancer tissue samples (see Examples below). By extension, it may be inferred that this nucleic produces elevated levels of encoded PD2 proteins which may also be used as pancreatic cancer markers.

As mentioned previously, cell lines expressing the PD2-encoding nucleic acids or variants thereof may be used in screening methods to identify agents which modulate PD2 function.

In one broad aspect, the present invention encompasses kits for use in detecting expression of PD2 in pancreatic tissues. Such a kit may comprise one or more pairs of primers for amplifying nucleic acids corresponding to the PD2 gene. The kit may further comprise samples of total mRNA derived from tissue of various physiological states, such as normal, early stage and metastatically progressive tumor, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting pancreatic cancer cells in a biological sample comprising oligonucleotide probes effective to bind with high affinity to PD2 mRNA in a Northern blot assay and containers for each of these probes. In a further embodiment, the invention encompasses a kit for use in detecting PD2 proteins in pancreatic cancer cells comprising antibodies specific for PD2 proteins encoded by the PD2 nucleic acids of the present invention.

The following protocols are provided to facilitate the practice of the present invention.

Cell Lines Utilized in Various Analyses

The cell line Panc 1 was obtained from American Type Culture Collection (ATCC), and comprises a poorly differentiated pancreatic adenocarcinoma cell line (2). The well differentiated pancreatic tumor cell line HPAF-CD11 was established at Duke University (3). The sources of other pancreatic cell lines of various states of morphological differentiation were: Colo 357, obtained from George Moore (Denver, Colo.); SW 979, Panc 89, and QGP-1 from H. Kalthoff (Hamburg, Fed. Rep. of Germany). The following cell lines were obtained from ATCC: Pancreatic tumor cell lines Hs 766T, AsPc-1, BxPc-3, Mia Paca, Capan-1, HGC 25; Human B lymphocyte cell line NALM; NIH3T3 and the SK-MEL-28 melanoma. Human foreskin fibroblast cells (HUFF) were obtained from primary cultures established by Dr. Kay Singer, Duke University Medical Center. Cell lines were cultured in Dulbecco's modified Eagle's medium supplemented with 10% fetal calf serum. Normal pancreata were obtained from Duke University Comprehensive Cancer Center and the University of Nebraska Medical Center tumor and tissue banks using standard procedures.

RNA and DNA Purification

Total cellular RNA from various tumor cell lines was isolated by the guanidine isothiocyanate-cesium chloride cushion ultra centrifugation method (4). Cells were washed twice with ice cold phosphate buffered saline and lysed with a solution containing 4 M guanidine isothiocyanate, 0.05 M sodium acetate, 250 mM 2-mercaptoethanol. Total RNA was recovered via sedimentation through a 5.7 M CsCl, 0.025 M sodium acetate cushion in a Beckman SW 40 Ti rotor centrifuged at 32,000 rpm for 18 hours. RNA pellets were resuspended in 0.3 M sodium acetate and precipitated with ethanol. Poly(A+) mRNA was further purified on two cycles of oligo (dT) cellulose affinity chromatography. Genomic DNA from HPAF/CD-11 and Panc 1 cell lines was purified by the SDS-Proteinase K digestion method and then extracted with phenol/chloroform.

Differential Screening and Cloning of PD2 cDNA

The Panc 1 cDNA library was subjected to differential hybridization using single stranded cDNA probes made from mRNA of Panc 1 and CD-11 cells. The probes were synthesized using mouse mammary leukemia virus (MMLV) reverse transcriptase (BRL, Gaithersburg, Md.) and random hexamer primers (Pharmacia, Piscataway, N.J.). The reaction was carried out in 50 µl of buffer containing 50 mM Tris pH 8.3, 75 mM KCl, 10 mM DTT, 3 mM MgCl, 3 µg random hexamer primers, 200 µM DATP, 20 µM unlabelled dCTP, 200 µM dTTP, 40 µCI $\alpha$-$^{32}$P-dCTP, 5 µg actinomycin D, 45 units of RNasin (Promega Biotec, Madison, Wis.), and 300 units of MMLV reverse transcriptase. Following incubation at 37° C. for one hour, the reaction was stopped by adding EDTA to 20 mM, and fragments larger than 100 bp were separated by Sephadex G-100 chromatography. RNA in the cDNA-RNA hybrid was hydrolyzed at 65° C. for 30 minutes in an equal volume of 0.6 N NaOH and 30 mM EDTA. The specific activity of cDNA obtained was 0.5 to 1.5×10$^8$ cpm/µg of RNA. For screening, triplicate nitrocellulose membranes were lifted and subjected to alkaline hydrolysis and neutralization. Prehybridization, hybridization and washing were as previously described (5–7). Plaques which hybridized strongly with the Panc 1 cDNA probe, but not with the HPAF/CD-11 cDNA probe, were selected. The differential reactivity was confirmed through at least two additional screening cycles.

Using a DNA insert derived from a differentially expressed cDNA clone, five additional cDNA clones were isolated from a normal human fetal pancreatic cDNA library.

Sequencing Analysis of PD2 cDNA

Single phage plaques selected after differential screening were grown to large quantities using either plate lysates or liquid culture followed by glycerol gradient purification (5). EcoRI inserts from purified DNA were subcloned into pBluescript +/− vectors (pBS) (Stratagene, La Jolla, Calif.). Both single stranded and double stranded templates were sequenced. Single stranded cDNA was prepared using standard techniques with the + and − strand pBS phagemids that are hybrid for f1 phage and pBS (Stratagene). Sequencing was performed by specific primer extension using Sequenase T4 DNA polymerase under conditions recommended by the supplier (U.S. Biochemicals, Cleveland, Ohio). The entire cDNA was sequenced twice, in both directions.

In Vitro transcription and Translation of PD2 cDNA

PD2 cDNA was subcloned into pBS (Stratagene) in both orientations at the EcoRI site. The recombinant plasmid was linearized with HindIII, extracted with phenol: chloroform and ethanol precipitated. Linear plasmids containing inserts in both orientations were transcribed using T7 polymerase following the instructions of the supplier (Promega). The transcripts were translated in a rabbit reticulocyte lysate (Promega) using the manufacturer's procedure with 50 µCi of $^{35}$S-methionine (Amersham). The products were separated by electrophoresis on either 7.5% or 10% SDS polyacrylamide gels, and visualized by autoradiography. Fluorography was used to enhance the radioactive signal using EN3'HANCE (DuPont-NEN).

Northern and Southern Blot Analysis

Total RNA (20 µg) and/or purified poly (A) RNA were fractionated by electrophoresis on 1.2% agarose gels containing 0.66 M formaldehyde and transferred to nitrocellulose via capillary blotting. Genomic DNA was digested with the indicated restriction enzymes and separated on 0.8% agarose gel electrophoresis. Southern blotting was performed using standard procedures (5–7). cDNA probes were labeled with $^{32}$P dCTP using a random-primed labeling kit (Boehringer Mannheim, Indianapolis, Ind.), and were separated from free label by Sephadex G-50 column chromatography (Pharmacia). Prehybridization and hybridization for both Northern and Southern blots were carried out in a solution of 5×SSPE, 50% formamide, 5× Denhardt's reagent, 200 µg/ml of sheared salmon sperm DNA and a minimum of 106 cpm/ml of probe at 42° C. for 18 hours. Blots were washed twice with 2×SSC containing 0.1% SDS at room temperature for 15 minutes followed by 4 washes with 0.2×SSC, 0.1% SDS at 60° C.

Sequence Analysis and Molecular Modeling

Primary cDNA and deduced amino acid sequence information was analyzed for homology with previously described molecules using the GCG software analysis program (version 7, Genetics Computer Group, Madison, Wis.), and MacVector 3.5 (International Biotechnologies, Incorporated, New Haven, Conn.). FASTA searches for similarity were performed using the following databases: GENBANK (75.0), EMBL (33.0) and Swissprot (24.0).

The Molecular Modeling Core Facility at the Eppley Institute, UNMC, was used for visualizing the crystallographic structure of proteins with homology to PD2. These included coordinates for aspartate amino-transferase (1AAT, Protein Data Bank, Brookhaven National Laboratory) and glutaminyl tRNA synthetase bound to its cognate tRNA (1GSG, Protein Data Bank, Brookhaven National Laboratory). The structures were visualized on a Silicon Graphics work station using Sybyl software, developed by Tripos Associates, St. Louis, Mo.

Chromosomal Mapping

The chromosomal localization of the PD2 gene was performed using the gene-based sequence-tagged-site (STS) mapping method as published earlier (8). The 3'-untranslated region (UT) of the PD2 cDNA sequence was used to design primers for PCR screens of both CEPH megabase-insert YAC DNA pools, obtained from Research Genetics, Huntsville, Ala. (9), and Coriell human x rodent somatic cell hybrid DNA pools (10). For PCR amplification, 4 µl of YAC pool DNA was used in a 15 µl reaction with 250 µm each DNTP, 100 ng of each primer and 0.4 U of AmpliTaq polymerase in GeneAmp reaction buffer. Reactions were cycled in a Perkin Elmer Gene Amp PCR system 9600 as follows: 4 minutes at 94° C.; then 35 cycles of 15 seconds at 94° C., 1 minute 15 seconds at 55° C., 1 minute 15 seconds at 72° C. followed by an extension step of 10 minutes at 72° C. The same set of primers and conditions were used to screen the somatic cell hybrid panel DNA, NIGMS #1, from Coriell Institute for Medical Research (Camden, N.J.).

Transfection of NIH3T3 Cells with PD2 Sense and Antisense Constructs

The PD2 cDNA was cloned at the EcoRI site of the pcDNA3.1 vector in the sense and antisense orientation. The recombinant constructs were transfected into NIH3T3 cells using the Lipofectamine method (GIBCO, BRL).

The examples presented below are provided to illustrate certain embodiments of the invention. They are not intended to limit the invention in any way.

EXAMPLE I

Figure 1B:
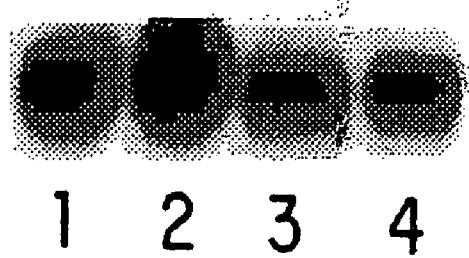

Isolation and Sequencing of a cDNA Differentially Expressed in Pancreatic Adenocarcinomas Isolation of cDNA A cDNA library from a poorly differentiated human pancreatic tumor cell line, Panc 1, was screened for differentially expressed mRNAs using single stranded cDNA probes synthesized from mRNA from the well-differentiated HPAF-CD11 (3) and poorly differentiated Panc 1 (2) human pancreatic tumor cell lines. Seventeen clones were obtained that hybridized very strongly to the Panc 1 probe and did not hybridize to the HPAF/CD-11 probe. The characterization of two of these clones has previously been published: one encoded the human ribosomal protein S16 (2); the other (named PD-1) encoded the human ribosomal protein rpL17 (6). The cDNA reported here is named pancreatic differentiation 2 (PD2). A representative Northern blot is shown in FIG. 1A in which the PD2 cDNA insert hybridized to a 1.9 kb mRNA transcript. A comparison of PD2 mRNA levels in these cell lines reveals that PD2 is expressed at 30-fold higher levels in Panc 1 when compared to HPAF/CD-11 as determined by densitometric analysis. The same filter was probed with a human β-actin cDNA as a control for the quality and quantity of mRNA (FIG. 1B). Five additional PD2 cDNA clones were obtained from a normal fetal pancreatic library.

Sequence of the PD2 cDNA

All cDNA clones isolated from the Panc 1 cDNA library and from the normal fetal pancreatic cDNA library showed 100% identity in sequence. The complete nucleotide sequence and the deduced amino acid sequence of the longest PD2 cDNA (1.9 kb) are shown in FIG. 2. The cDNA sequence contained a 5' untranslated region of 156 base pairs and a 3' untranslated region of 138 bp. The non-coding 3' region contained the polyadenylation signal AATAAA as underlined in FIG. 2. An open reading frame from nucleotide 157 to nucleotide 1752 yields a predicted translation product of approximately 60 kDa. A search of the GENBANK and EMBL databases revealed that PD2 is a newly identified sequence, as the nucleotide sequence of PD2 did not show identity to any other deposited sequence.

Characterization of the PD2 cDNA

Figure 3:
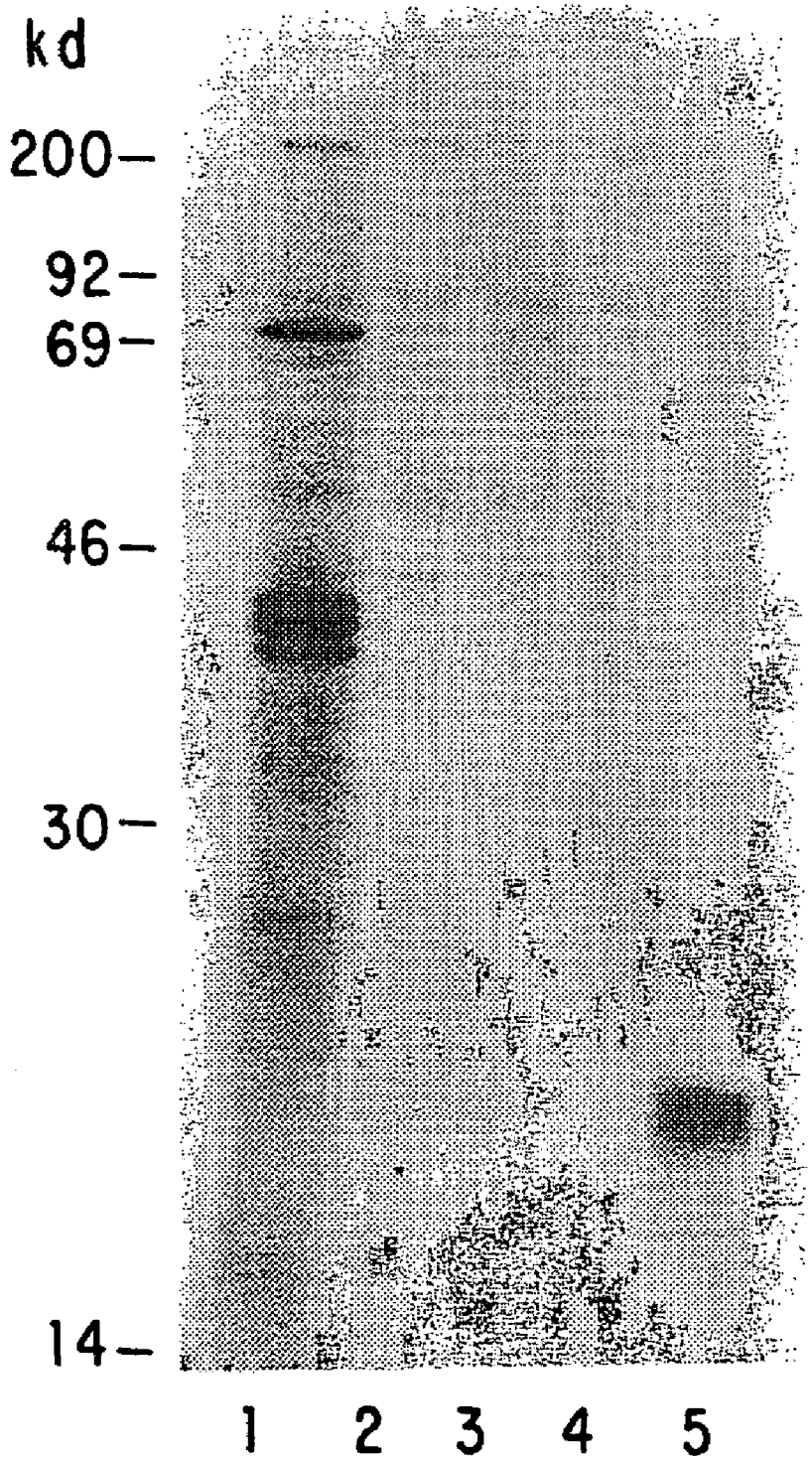
FIG. 3 depicts the in vitro transcription/translation product of PD2 cDNA. RNA transcripts were generated from pBluescript using T7 RNA polymerase and translated in rabbit reticulocyte lysate in the presence of $^{35}$S methionine. The protein products were separated by SDS-polyacrylamide gel electrophoresis and visualized by autoradiography. The DNA constructs used to generate the transcription/translation products or the negative controls were as follows: lane 1, PD2 cDNA inserted in pBluescript in the sense orientation; lane 2, PD2 cDNA inserted in pBluescript in the antisense orientation; lane 3, pBluescript linearized with HindIII; Lane 4, control rabbit reticulocyte lysate containing no exogenous transcripts; Lane 5, construct containing cDNA for PD-1 in the sense orientation.

The PD2 mRNA transcript was expressed using T7 RNA polymerase and translated in rabbit reticulocyte lysate in the presence of $^{35}$S methionine. The in vitro translation products were analyzed by 7.5% SDS-PAGE and the results are shown in FIG. 3. When PD2 cDNA was placed in the correct orientation, a protein of approximately 70 kDa was also seen along with three other protein bands of about 43 kDa, 44 kDa, and 45 kDa (lane 1). This pattern of reactivity was seen when non-reducing SDS-PAGE gels were run on these samples (data not shown). Similar products were not produced in lysates that contained linear pBS DNA cut with Hind III (lane 3), full length PD2 in an antisense orientation, (lane 2) or lysate alone (lane 4). A positive control for in vitro transcription/translation analysis using the unrelated cDNA clone PD-1 (6) showed translation of a protein with the expected size of 17 kDa. The discrepancy between the observed migration of PD2 (70 kDa) and several smaller species and the calculated mass (60 kDa) may be due to posttranslational modification in the reticulocyte lysate or intrinsic properties of the protein. It is unlikely that the different protein forms are consequences of mutations in the insert that alter the reading frame, or contaminated plasmid preparations, since three independent preparations from a single colony gave essentially the same pattern (data not shown).

Chromosomal Localization of the PD2 Gene

The PD2 gene was mapped to the short arm of chromosome 19 (19p13.11-q11). This location was obtained by linking the YAC that PD2 mapped to (CEPH 785_d__8) out four levels to another YAC (CEPH 968_g_5). This YAC then had an sequence-tagged-site (STS) (D19S215) mapped to it, which is mapped to Genethon position 0.38 on Chromosome 19. This position could not be translated to the cytogenetic map because a map for chromosome 19 is not yet available for this region. However, the STS (D19S215) has been mapped on the Lawrence Livermore National Laboratories physical map of chromosome 19 about 20 Mb from the p-ter. Using the sizes of the four YACs that link PD2 to this STS, a region of 19p13.11-q11 was determined.

EXAMPLE II

Characterization of the PD2 Protein

Functional Motifs in the PD2 Prot in

A search for protein motif similarities in the GENBANK, EMBL, PDB and Swiss Prot databases, using BLAST and the FASTA program of the GCG sequence analysis software package, revealed that the PD2 protein has some regions of similarity to several known proteins (Table I).

TABLE I

Proteins with partial homology to PD2

| PROTEIN | ACCESSION NUMBER* | POSITION AND PERCENTAGE IDENTITY |
|---|---|---|
| Yeast transcriptional factor PAFI | P38351 | 277–336, 26% in 60 residues |
| INCENP nuclear protein | P53352 | 103–192, 23% in 90 residues |
| Glucokinase | pdb/lglk/80 9431 | 243–280, 36% in 38 residues |
| E. coli valyl tRNA synthetase | P07118 | 36–133, 25% in 98 residues |
| RNA polymerase sigma 54 factor | p2469 | 68–100, 24% in 33 residues |
| Yeast ATP dependent RNA helicase | P15424 | 145–159, 47% in 15 residues |
| Yeast Myosin-like protein MLPI | Q02455 | 59–93, 37% in 35 residues |
| E. coli Aspartate Aminotransferase | P14909 | 200–270, 27% in 71 residues |
| Simian immunodeficiency virus reverse transcriptase | P5896, P5897, P19509 | 295–326, 38% in 32 residues |
| | P112502 | 318–364, 24% in 47 residues |
| Murine leukemia virus reverse transcriptase | P11227, P03355, P03357 | 236–271, 27% in 37 residues |
| Recombinase flp protein | P13784 | 300–339, 23% in 40 residues |
| Trypanosome RNA polymerase | P16355 | 313–366, 19% in 54 residues |
| cAMP dependent protein kinase, type 1 regulatory protein | PP12849 | 263–345, 23% in 83 residues |
| Modification methylase RSR1 | P14571 | 312–363, 27% in 52 residues |
| Maternal effect protein oscar (Drosophila) | P25158 | 117–176, 26% in 63 residues |
| Inclusion body matrix protein (Viroplasmin) | P09524 | 125–184, 20% in 67 residues |

*Accession numbers are from Swissprot (P and Q), PDB, and EMBL databases, References of each of the sequence is available in the databases.

Some of the regions with identity coincide with functionally important regions of proteins, including a yeast transcriptional factor (11); INCENP nuclear protein (12); Glucokinase (13); valyl-tRNA synthetase (14); aspartate amino transferase (15); the cAMP binding domain of the bacterial Catabolite Activator Protein (16); and eukaryotic regulatory type I subunit of a cAMP-dependent protein kinase (17). There is also similarity with certain functionally important regions of several other proteins with known biological activity that are shown in Table I.

Figures 4A, 4B:
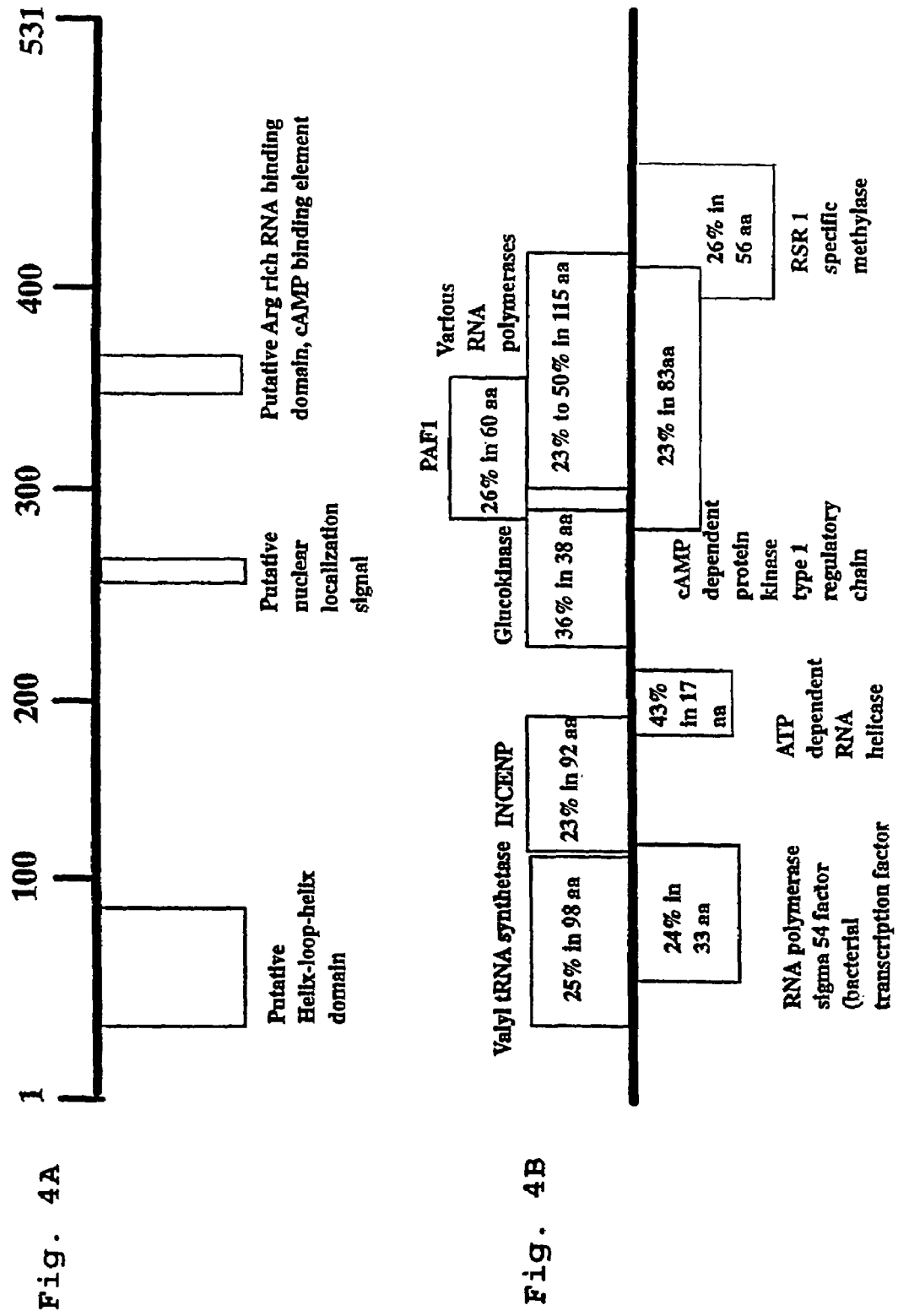
FIGS. 4A and 4B schematically represent the PD2 primary amino acid sequence, from amino acid 1 through 531.

The PD2 protein depicted in FIGS. 4A and 4B contains the following motifs, a putative nuclear localization signal (KKRK) at residues 269–272 (18); a putative arginine rich RNA binding domain (RVRLSKRRAKA; SEQ ID NO: 14) at residues 329–339 with homology to a consensus sequence described in reference (19); and a putative helix-loop helix domain near the amino terminus with homology to a family of helix-loop-helix (HLH) proteins described previously (20) that include members of the myc and myo D families, and several HLH proteins that play important roles in Drosophila development. FIG. 5 shows the alignment of HLH domain of PD2 with the HLH domain in Drosophila hairy protein, a negatively acting member of this family that regulates expression of other genes involved in segmentation and bristle pattern development (21). Some members of this family of proteins contain a basic region important for DNA binding which precedes the first helix. The HLH domain itself has been shown to be required for heterodimerization of these family members with other proteins. Some negatively acting HLH proteins that associate with and block the action of positively acting HLH proteins lack the basic region preceding the HLH domain, or contain prolines in their basic region (20). The PD2 protein is similar to the latter of these, in that it contains prolines and several basic residues in the region immediately preceding the putative HLH domain (residues 11–24). See FIG. 5.

Another region of PD2 (residues 263–345, 23% in 83 residues, FIG. 4) demonstrated significant homology with the type I regulatory chain of an intracellular cAMP dependent protein kinase (residues 265–343,) (17). The region of homology fell within one of the two cAMP binding domains of the regulatory chain of this enzyme. Furthermore, the PD2 amino acid sequence showed significant homology with the conserved residues found in the cAMP binding site of the E. coli catabolite activator protein (16) and both of the cAMP binding sites found in the regulatory chain of the eukaryotic protein kinase, that included critical glutamic acid and arginine residues known to be important in forming hydrogen bonds involved in binding the cAMP and forming the pocket around it (16). See FIG. 6. The biological relevance of this region of homology with the cAMP binding element is further supported by the fact that an overlapping sequence (described below) showed homology with an arginine rich motif found in several potential RNA binding proteins (19). PD2 also contained several phosphorylation sites similar to histone kinase and casein kinase.

PD2 Prot in in the Cell

To study the production of PD2 protein and examine its localization within the cell, polyclonal antibodies were generated against two synthetic peptides of the deduced amino acid sequence of PD2. The peptides were selected based on their high antigenic index as analyzed by the MacVector Program. PD2 Peptide 1 (PD2 μl) corresponds to amino acids 142–162 and has the following sequence:

NH$_2$-RYGISNEKPEVKIGVSVKQQF-COOH    (SEQ ID NO: 10)

PD2 peptide (PD2p2) corresponds to amino acids 327–348 and has the following sequence:

NH$_2$-ETRVRLSKRRAKAGVQSGTNAL-COOH    (SEQ ID NO: 11)

Figure 7:
FIG. 7 depicts immunoblotting analysis of cytoplasmic and nuclear protein fractions from Panc 1 and HPAF/CD11 cells. Equal amounts of cytoplasmic and nuclear protein lysates from each cell line were loaded onto an SDS-PAGE gel and electroblotted onto nitrocellulose. The PD2p2 polyclonal antibody reacted with a band of about 70 kd and 3 smaller fragments of approximately 40–45 kd in the nuclear extracts isolated from both Panc 1 and HPAF/CD-11 cells.

The peptides listed above were conjugated to KLH and the resulting immunogen used to immunize rabbits. Serum was then isolated from a rabbit immunized with PD2p2 peptide and PD2 antibodies purified using peptide affinity chromatography. The antibodies were then used as probes for Western blotting of cytoplasmic and nuclear extracts from HPAF/CD11 and Panc1 cells. The PD2p2 antibody reacted with a protein of approximately 70 kd in nuclear extracts from both cell lines. The intensity of the PD2 protein band in the nuclear extract was 30 fold higher in Panc1 cells as compared to HPAF/CD11 cells. See FIG. 7. A similar level of over expression was seen in PD2 mRNA and gene copy number in the Panc1 line.

EXAMPLE III

Role of PD2 in Differentiation and Tumor Progression Differential Expression of PD2

Figure 8A:
FIGS. 8A and 8B are autoradiographs depicting Northern blot analyses of total RNA (20 μg/lane) from a panel of pancreatic carcinoma cell lines. Total RNA was fractionated by electrophoresis on 1.2% agarose/formaldehyde gel and transferred to a nitrocellulose membrane. Pancreatic carcinoma cell lines analyzed were as follows: Colo 357 (lane 1), Fa-2C (lane 2), Panc 89 (lane 3), Panc 1 (lane 4), Capan 2 (lane 5), HS 766T (lane 6), SW 979 (lane 7), T3M4 (lane 8), HPAF (lane 9), BxPC 3 (lane 10), AsPC 1 (lane 11), QGP-1 (lane 12), MiaPaCa (lane 13) and HGC-25 (lane 14).
Figure 8B:
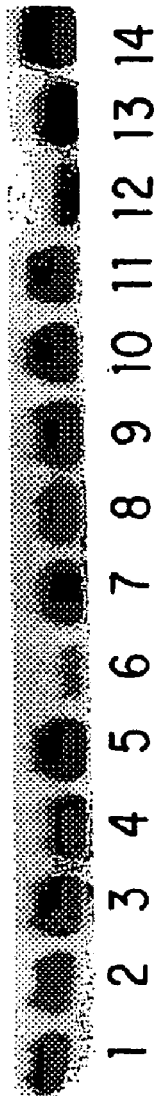

Expression of the PD2 gene was evaluated further in a panel of 14 pancreatic tumor cell lines representing various morphological stages of differentiation. The putative differentiation grade for the various tumor cell lines was determined from the published morphological and ultrastructural descriptions of the cell lines and corresponding tumors (22). Total RNA from these tumor cell lines were fractionated, Northern blotted and probed with PD2 cDNA. The results of this experiment are shown in FIG. 8A. The PD2 cDNA probe hybridized to a message size of approximately 1.8 kb in all cell lines, but its expression was significantly elevated only in Panc 1. FIG. 8B shows rehybridization of the same filter with a β-actin probe confirming equal loading of the gel.

Figure 9A:
FIGS. 9A and 9B are autoradiographs depicting Northern blot analysis showing expression levels of PD2 mRNA in normal and tumor cell lines and tissues. Total RNA (20 μg/lane) was fractionated by electrophoresis on a 1.2% agarose/formaldehyde gel and transferred to a nitrocellulose membrane. The cell lines and tissues examined were: pancreatic tumor cell lines Panc 1 (lane 4) and HPAF (lane 3); breast carcinoma cell lines BT 20 (lane 1) and CAMA-1 (lane 2); colon carcinoma cell lines LS 180 (lane 6) and Colo 320 (lane 7); normal human pancreas (lane 5); tail portion of pancreas (lane 8); pancreatic tumors (lanes 9, 10 and 11); normal human foreskin fibroblasts (lane 12); and human B lymphocyte cell line NALM (lane 13).
Figure 9B:
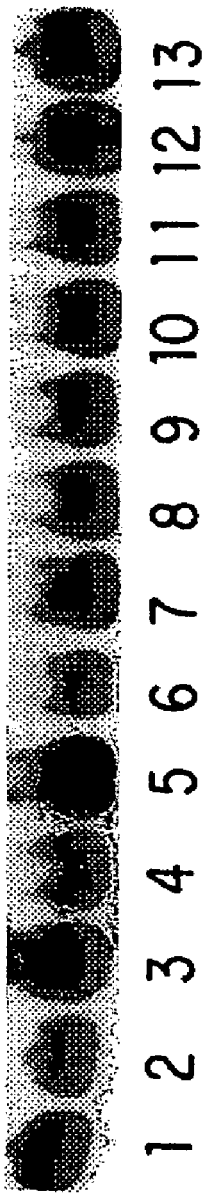

Expression of PD2 mRNA was also evaluated in colon and breast tumor cell lines, human foreskin fibroblasts, a Human B lymphocyte cell line and normal pancreatic tissues. The results, shown in FIG. 9A, revealed relatively low levels of mRNA transcripts for PD2 in all cell lines examined except Panc 1. FIG. 9B is a control blot showing equal loading of RNA.

Differential Amplification of the PD2 Gene

Figure 10:
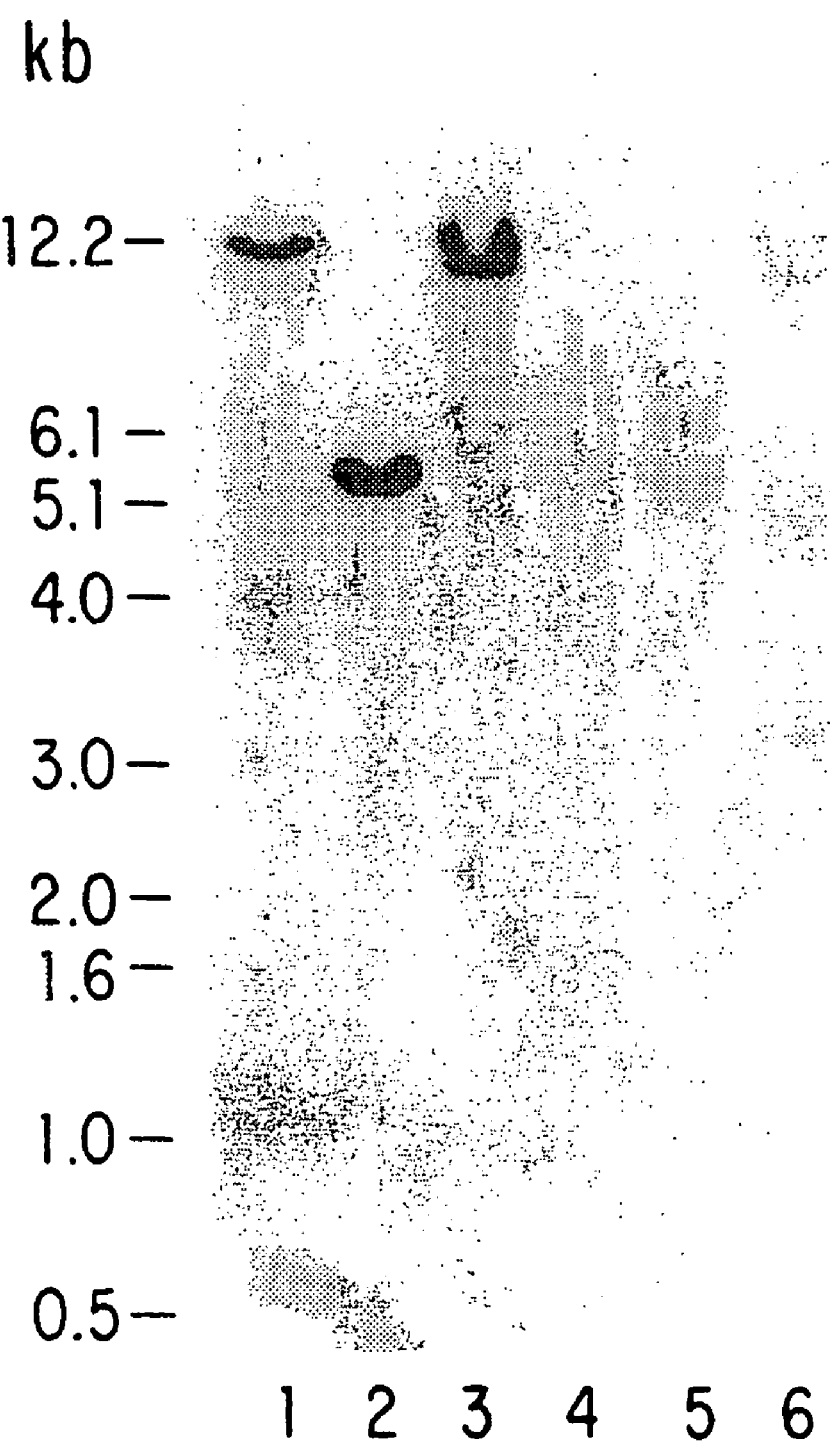
FIG. 10 is an autoradiograph of Southern blot analysis of genomic DNA (10 μg/lane) from the Panc 1 and HPAF/CD11 pancreatic tumor cell lines. After restriction endonuclease digestion, the DNA was electrophoretically separated on a 0.8% agarose gel and transferred to a nitrocellulose membrane by standard methods. Lanes 1, 2 and 3 contained Panc 1 DNA digested with EcoRI, HindIII and BamHI, respectively. Lanes 4, 5, and 6 contained HPAF/CD11 DNA digested with EcoRI, HindIII and BamHI, respectively. The blot was probed with a $^{32}$P-labelled PD2 cDNA probe, revealing the 30-fold amplification of the PD2 gene in Panc 1 cells as compared to HPAF/CD11.
Figure 11:
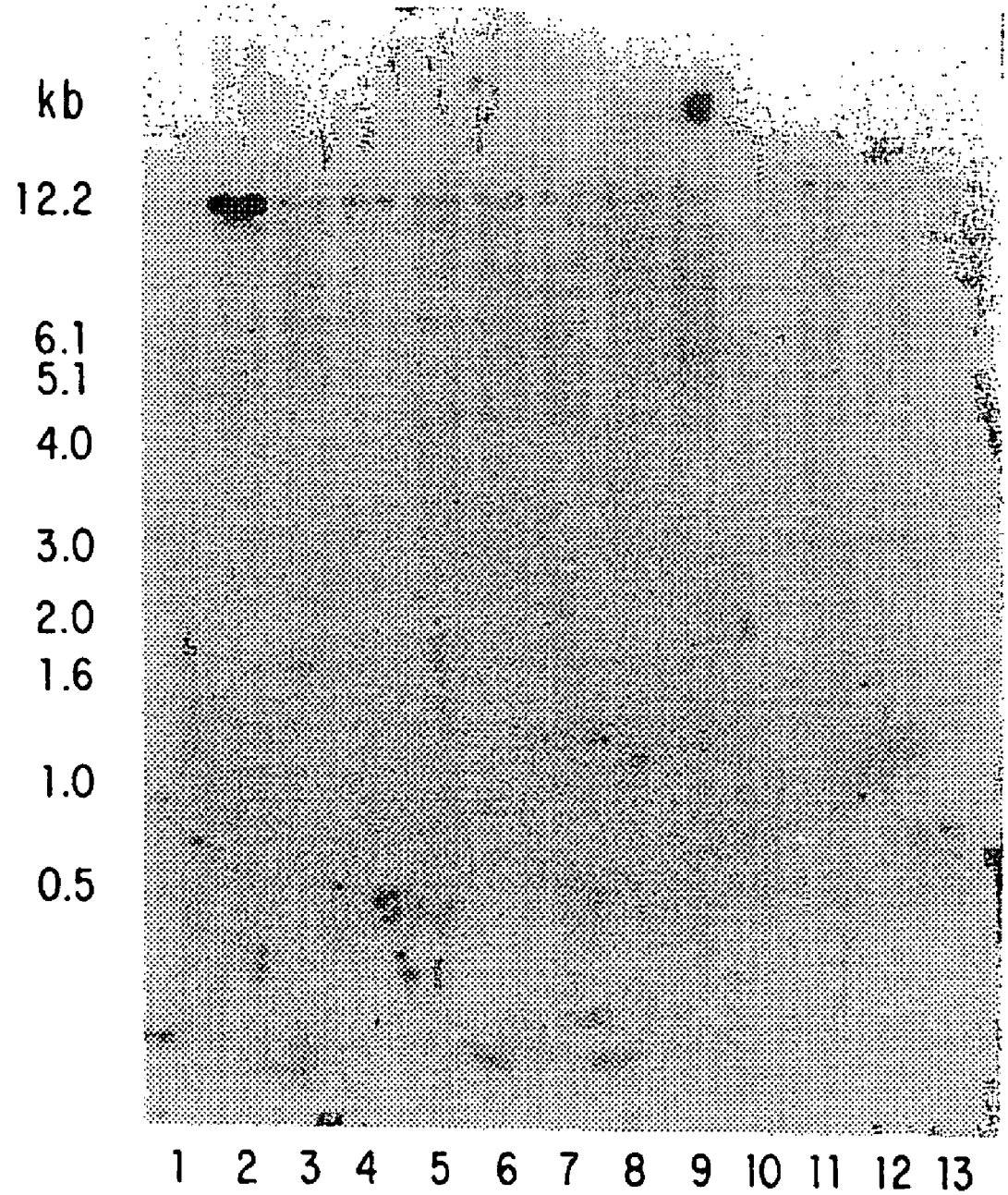
FIG. 11 is an autoradiograph showing results from Southern blot analysis of genomic DNA (10 μg/lane) from a panel of tumor cell lines. After restriction endonuclease digestion with EcoRI, the DNA was electrophoretically separated on a 0.8% agarose gel. Cell lines analyzed included: pancreatic cell lines HPAF/CD11 (lane 1), Panc 1 (lane 2), Colo 357: (lane 3), SW 979 (lane 4), Capan-1 (lane 5), T3M4 (lane 6), and Hs 766T (lane 7); breast cancer cell lines: CAMA-1 (lane 8), MCF-7 (lane 9), Sk-BR (lane 10). Colon carcinoma cell lines: WiDr (lane 11), Colo 320 (lane 12) and LS 180 (lane 13). The blot was probed with $^{32}$P labelled PD2 cDNA.

Purified genomic DNA from the poorly differentiated cell line Panc 1 and well differentiated cell line HPAF/CD 11 were digested with EcoRl, BamHl and Hindlll, fractionated by agarose gel electrophoresis, Southern blotted and hybridized to the PD2 cDNA probe as shown in FIG. 10. The probe hybridized to two or more fragments raising several possibilities. PD2 could be part of multi-gene family, there may be pseudogenes for PD2, or PD2 is a part of large gene that contains multiple restriction sites. One of the bands showed a 30-fold amplification in Panc 1 DNA as compared to HPAF/CD11, suggesting that this corresponds to the gene encoding the transcribed product seen in Panc 1 cells. Furthermore, Southern blot analysis of EcoRl-digested DNA from a large panel of tumor cell lines including six pancreatic tumor cell lines, three breast tumor cell lines and three colon tumor cell lines confirmed that amplification of the PD2 gene occurred only in the Panc 1 cell line as shown in the FIG. 11.

Figure 12:
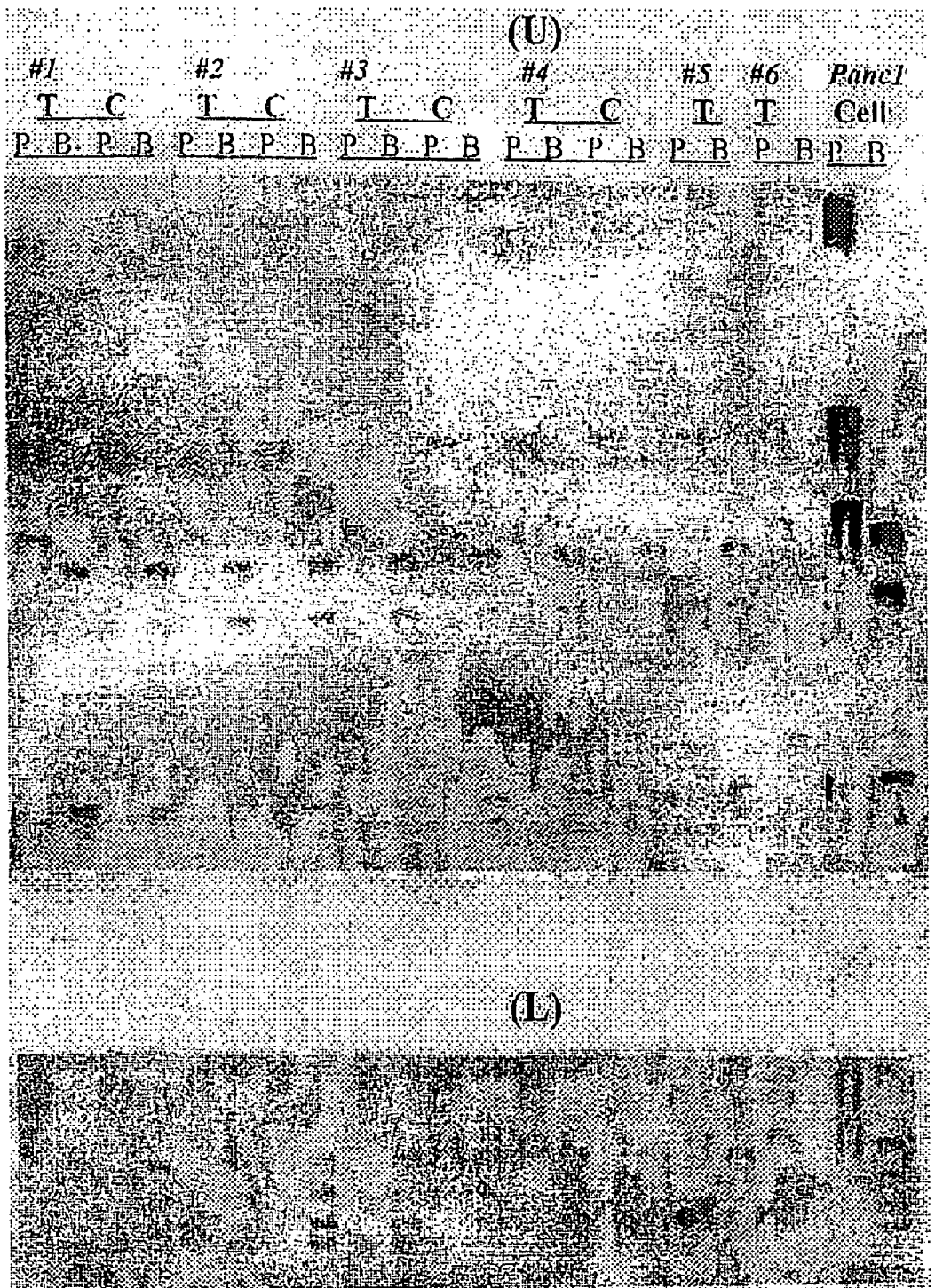
FIG. 12 is an autoradiograph illustrating that the PD2 gene is amplified in human pancreatic biopsies and tumor cell lines. Purified DNA (10 μg) was digested with PstI (P) and BglII (B), fractionated on 8% agarose and transferred to a nylon membrane. The blot was probed with a $^{32}$P-labelled probe specific for PD2 (upper panel). The same blot was stripped and rehybridized to a control probe to confirm equal loading in each lane. Tumor (T) and normal tissue adjacent to tumor (C). DNA from patient cases 1–4 are shown in lanes 1–16. Tumor DNA isolated from cases 5 and 6 are shown in lanes 17–20. Pancl DNA is shown in lanes 21 and 22.

Tumor specimens were assessed for the amplification of of the PD2 gene as shown in FIG. 12. One tumor biopsy sample also showed amplification of the PD2 gene. The same blot was stripped and reprobed to confirm equal loading of the lanes. These results demonstrate that PD2 is involved in the development of pancreatic cancer.

Figure 13:
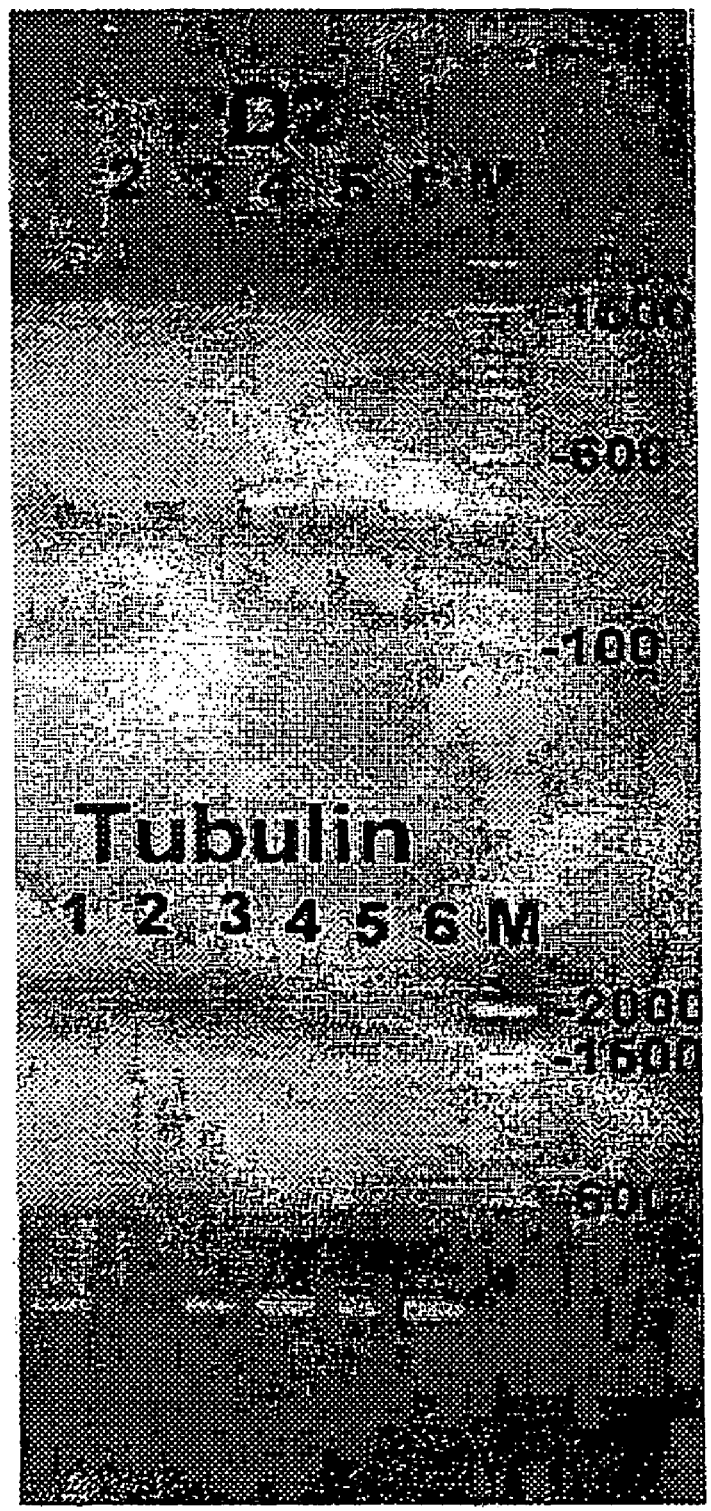
FIG. 13 is an an ethidium bromide stained gel showing the results of RT-PCR on normal human and adult pancreatic tissues. RT-PCR products from normal fetal and adult pancreas were fractionated on a 1.5% agarose gel. Lanes 1–3, adult pancreas; lanes 4–6, fetal pancreas; M, 100 base pair ladder.
Figure 14:
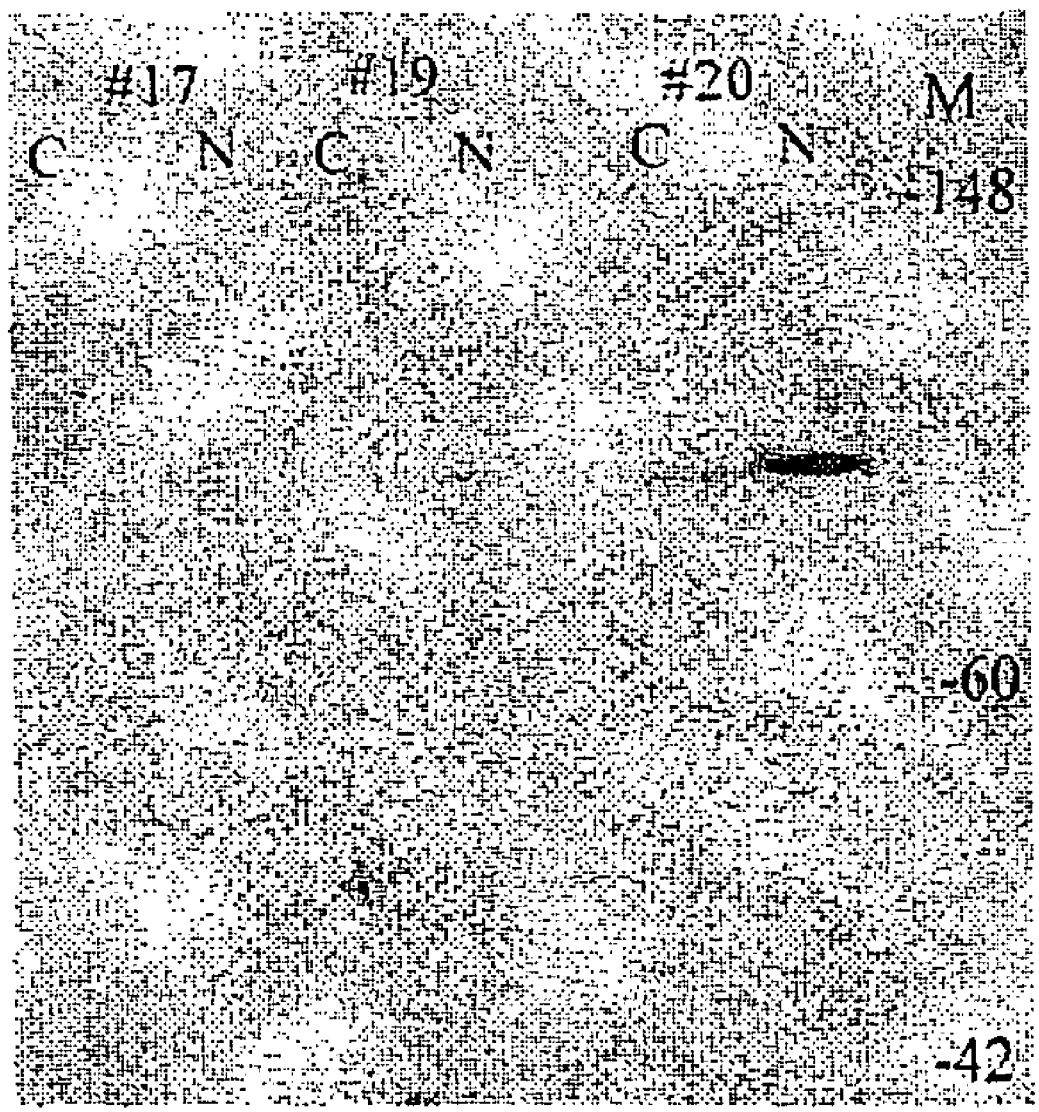
FIG. 14 depicts immunoblot analysis of the epitope-tagged PD2 protein. After transfection of the epitope-tagged PD2 cDNA construct in the pancreatic tumor cells, clones were isolated for G418 resistance. Lysates for three clones were analyzed. Protein bands were resolved by SDS-PAGE, transferred to nitrocellulose and probed with M2 monoclonal antibody which specifically recognizes the flag epitope. C, cytoplasmic lysate; N, nuclear lysate; M, molecular weight marker.
Figure 15:
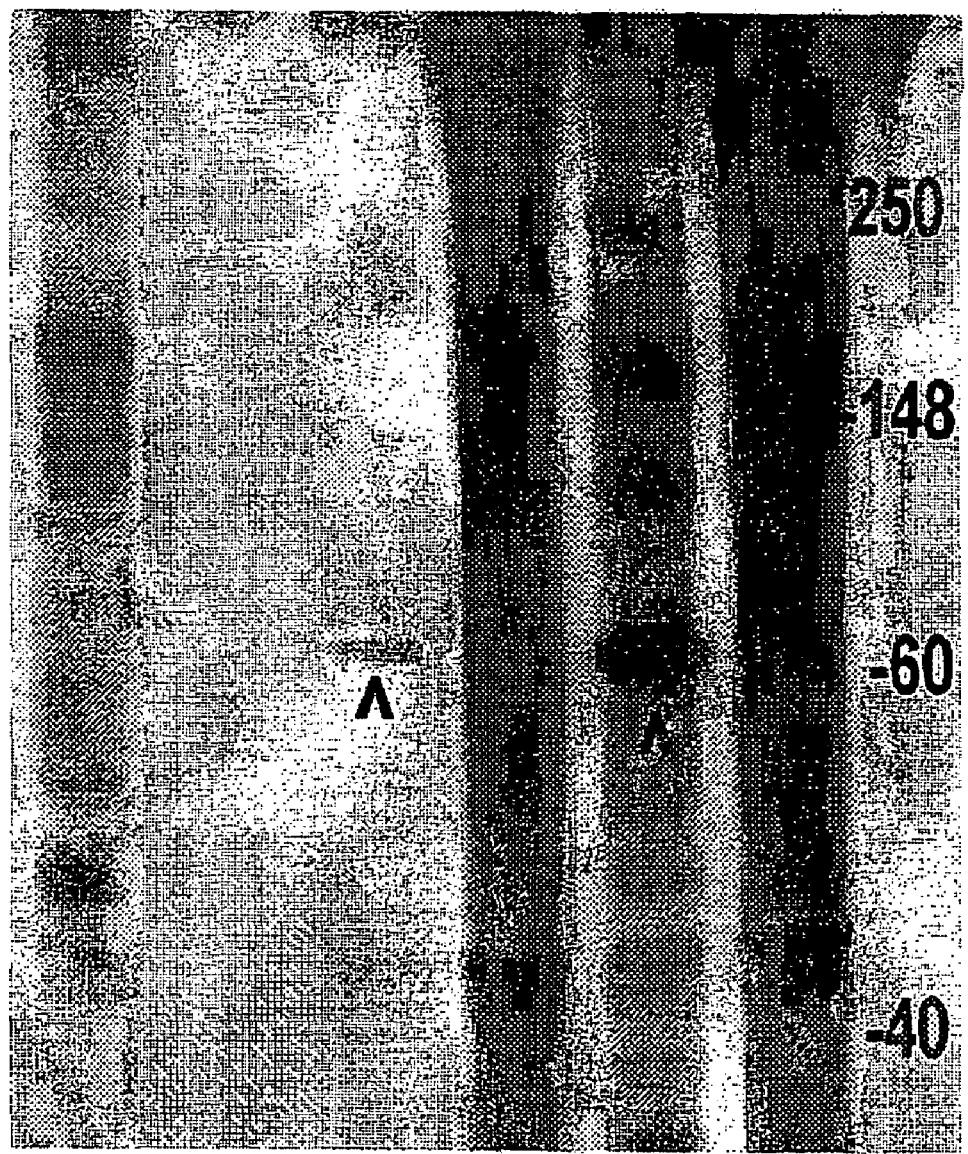
FIG. 15 shows an autoradiogram of a SDS-PAGE gel run under reducing conditions showing phosphorylation of PD2 protein in the presence of $^{32}$P orthophosphate. APR, vector alone; PD2F, APR vector with PD2 Flag sequences; C, cytoplasmic; N, nuclear.

The expression of the PD2 gene was also assessed in normal human adult and fetal pancreata. The results are shown in FIG. 13. Normal adult pancreas (ages 30–59) showed very low to undetectable levels of PD2 expression. However PD2 expression was consistently observed in all fetal tissues examined (age 18–24 weeks). Expression of the PD2 gene in fetal but not in adult pancreas further supports a role for PD2 in transformation and differentiation of pancreatic cells.

EXAMPLE IV

Expression Construct Analysis of PDZ

Construction of FLAG Epitope-Tagged PD2

A cDNA molecule was prepared which generated a fusion protein comprising PD2 and the Flag epitope. For this purpose, a double-stranded, synthetic oligonucleotide was designed to encode DYKDDDGSKSAIF which was inserted into the unique BglII site (bp 1511) of the PD2 cDNA. The in-frame insertion of the oligonucleotide was verified by sequence analysis.

FIG. 13 shows the results of Western blot analysis confirming expression and translation of the cDNA fusion construct. The results showed that epitope tagged PD2 protein is localized mainly in nuclear lysates.

Figure 16:
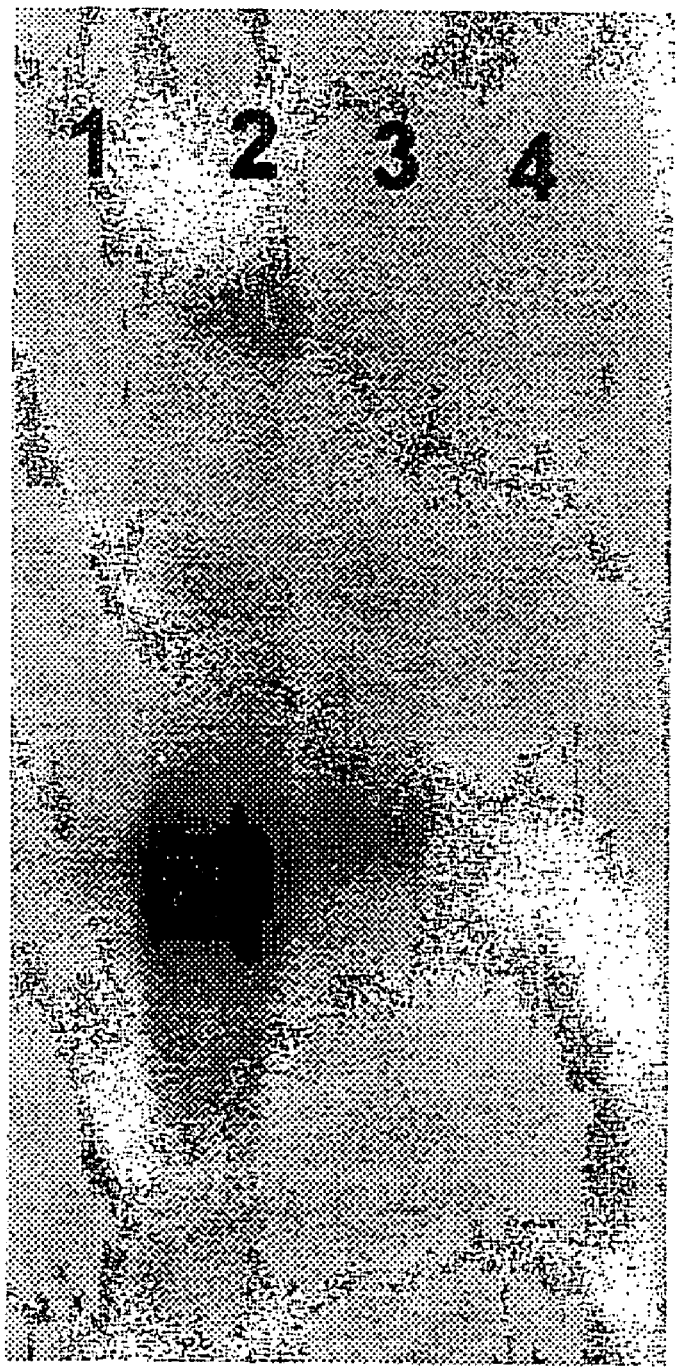
FIG. 16 is an autoradiogram showing the results of Northern analysis of transfected NIH3T3 cells. Total cellular RNA (10 μg) purified from human control and transfected cells was fractionated on a 1% agarose/formaldehyde gel, blotted, and hybridized with a cDNA probe to PD2.

In additional experiments, the 1.9 kb PD2 cDNA was placed under control of a strong CMV promoter by using the pCDNA3.1 vector for driving expression of PD2 in NIH3T3 cells. Stable transfectants were selected on geneticin (G418). Expression of PD2-specific mRNA in the NIH3T3 cells transfected with PD2 is shown in FIG. 16. There was no detectable mRNA for PD2 in the anti-sense PD2 transfected NIH3T3 cells, designated herein as PD2ASNIH3T3. NIH3T3 cells transfected with a sense construct, designated herein as PD2SNIH3T3, showed the expression of appropriate size mRNA for the PD2 gene.

Figure 17:
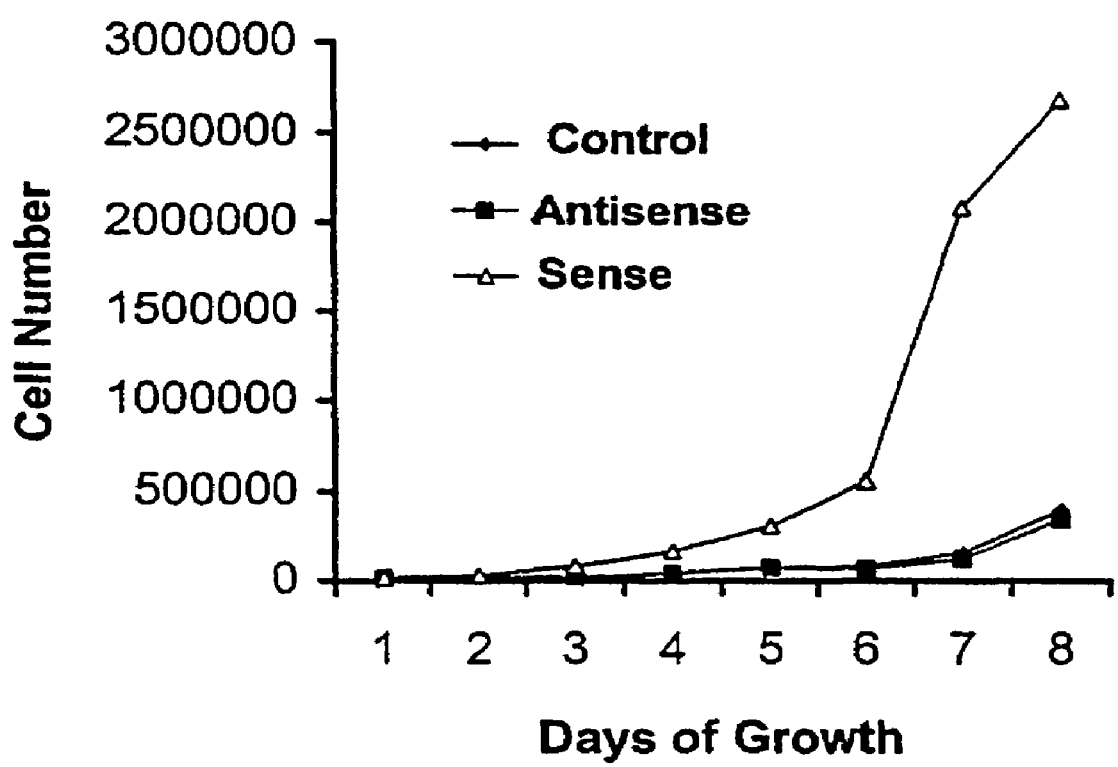
FIG. 17 is a graph showing the growth curve for PD2 transfected NIH3T3 cell lines.

Determination of growth kinetics revealed a shorter population doubling time for PD2SNIH3T3 cells as compared to PD2ASNIH3T3 cells or control, untransfected NIH3T3 cells. Viable transfected cells ($5\times10^3$) were plated in triplicate in RPMI medium with 10% fetal calf serum (Day 0). The following day the medium was changed and cells were harvested in 0.125% trypsin-0.02% EDTA every day and counted. FIG. 17 shows the mean values of three dishes over an 8 day time course. The data reveal that NIH3T3 cells expressing PD2 in the sense orientation divide more rapidly than control cells not expressing PD2 or cells expressing PD2 in an antisense orientation.

Figure 18:
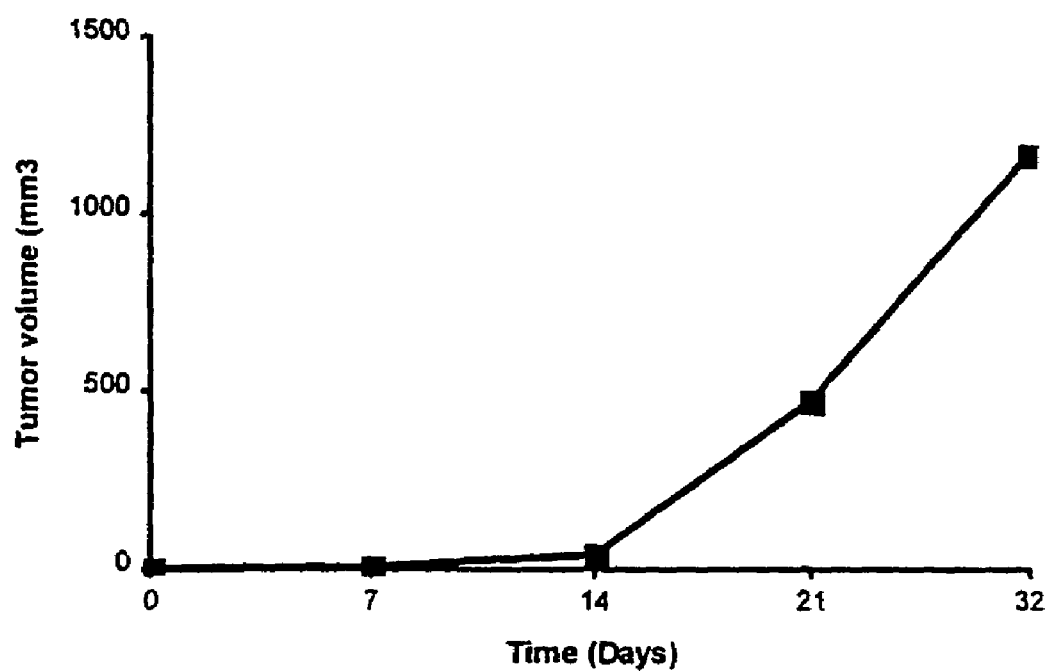
FIG. 18 is a graph showing the kinetics of tumor growth of PD2(sense)NIH3T3 cells inoculated into BALB/c nu/nu mice.

To investigate transformation properties of PD2SNIH3T3 cells in vivo, BALB/c, nu/nu were inoculated subcutaneously with PD2SNIH3T3, PD2ASNIH3T3 and control NIH3T3 cells. Groups of five mice were used and challenged with $1\times10^7$ cells of each cell type. Mice were palpated biweekly over a period of 5 weeks. The time to tumor formation(LP), the number of mice developing tumors, the doubling time of the tumors, and the size of the tumors were noted. Tumor volumes were calculated using width (a) and length (b) measurements ($a^2 \times b/2$, where a<b). PD2SNIH3T3 cells formed tumors in all mice after a latent period of 7 days, whereas no tumores developed in mice receiving identical doses of PD2ASNIH3T3 or NIH3T3 cells over an observation period of five weeks. See FIG. 18.

These results demonstrate that the PD2 gene can transform NIH3T3 cells and disturb the components that regulate growth rate in transfected cells.

EXAMPLE V

Genetic Testing of Tumor Biopsies for the Presence of PD2

As described in the previous examples, PD2 is overexpressed in pancreatic adenocarcinoma. The availability of the nucleic acids having the sequence of Sequence I.D. Nos. 1 as well as the primer sets set forth below provide reagents for genetic testing in patients for the presence or absence of amplified PD2.

```
PD2 forward primer:
5' TTCAGTCAGGCACCAACG 3'      (SEQ ID NO: 12)

PD2 reverse primer:
5' CGCTGGCCACCCCCATTG 3'      (SEQ ID NO: 13)
```

DNA may be isolated from biopsy samples. Such procedures are known to those of skill in the art. The DNA is suspended in 600 microliters of 50 mM NaOH in a 1.5 ml eppendorf tube. The tube is then vortexed for 10 seconds followed by a 5 minute incubation in a 95 degree hot water bath. Following this incubation, 60 microliters of Tris (1 mM, pH 8.0) is added to the tube and the sample vortexed for an additional 10 seconds. The tube is centrifuged in a microfuge for 1 minute to pellet the DNA. The supernatant is then discarded and the sample frozen or the DNA processed for PCR. Following DNA amplification, the DNA is sequenced in an automated DNA sequencer to confirm the results obtained with PCR.

EXAMPLE VI

Generation of a Hamster Model for Pancreatic Carcinogeneis

Little is known about the etiology, pathogenesis and molecular basis of pancreatic cancer (PC). Deletions, mutations, and rearrangements normally activate proto-oncogenes and inactivate anti-oncogenes (tumor-suppressor genes). These genetic alterations culminate in molecular events leading to deregulation of cell proliferation. Recent studies have shown that a preferred subset of normal genes is altered in human PC biopsies. Although alterations of these genes have been found in established tumors, nothing is known about early genetic events at the initiation stage of pancreatic carcinogenesis. Moreover, it is equally unclear whether alteration of one gene is sufficient or whether several simultaneous or a chain of multiple genetic abnormalities is required for the initiation of the uncontrolled growth.

It is well established that in the hamster pancreatic cancer model, which mimics the human is disease in many clinical and biological aspects, cancer develops not only from ductal/ductular cells but also from within islets, most probably from stem cells. The hormonal abnormalities found in more than 80% of pancreatic cancer patients, including development of diabetes and increased levels of insulin and islet amyloid polypeptide, ubiquitously reflect the involvement of the endocrine pancreas in the pathogenesis of the pancreatic cancer.

We have recently established an in vitro hamster islet culture, in which the stepwise cytological, immunohistochemical, cytogenetic and molecular biological changes could be followed. We have shown that these hamster pancreatic islet cells can be transformed in vitro by the pancreatic carcinogen, N-nitrosobis (2-oxopropyl)amine (BOP). After four weeks of treatment with BOP, the cultured islet cells showed accelerated growth and pleomorphism.

Anchorage independent and in vivo growth was not seen before week 19 of treatment. The mutation of the K-ras gene at codon 12 (GGT6GAT) was found at this stage. This abnormality is consistent with findings in over 90% of human and BOP-induced pancreatic cancer. In vivo, transformed hamster islet cells formed a poorly differentiated invasive cancer. Cytogenetic analysis of transformed hamster cells revealed deletions of chromosome Y and loss of heterozygosity of chromosomes 7 and 11. Hence, this system presents a unique model for elucidating stepwise early genetic alterations during pancreatic carcinogenesis.

Inasmuch as BOP triggers loss or inactivation of tumor suppressor genes, activation of oncogenes, and/or differential expression of tumor-associated genes in normal pancreatic cells at the initiation of carcinogenesis. The genetic alterations caused by these carcinogens appear to be critical in the development of pancreatic cancer.

This hamster model may be manipulated to assess the role of PD2 expression in the malignant transformation of the pancreas. Altered PD2 encoding nucleic acids may be introduced into these cells and effects of cell growth rates and morphology assessed. Additionally, the PD2 expressing cells may be treated with test compounds to identify those compounds which reverse the malignant phenotype. Such compounds may have beneficial therapeutic value in the treatment of pancreatic carcinomas.

REFERENCES

1. Liber, M., Mazzetta, J., Nelson-Rees, W., Kalpan, M., and Torado. (1975) Establishment of a continuous tumor cell line Panc1 from a human carcinoma of the exocrine pancreas. *Int. J. Cancer* 15, 741–747.
2. Batra, S. K., Metzgar, R. S. and Hollingsworth M. A. (1991) Molecular cloning and sequence analysis of the human ribosomal protein S16. *J. Biol. Chem.* 266, 6830–6833.
3. Kim, Y. W., Kern, H. F., Mullins, T. D., Koriwchak M. J., Metzgar R. S. (1989) Characterization of clones of a human pancreatic adenocarcinoma cell line representing different stages of differentiation. *Pancreas* 4, 353–62.
4. Chirgwin, J. M., Przybyla, A. E., MacDonald, R. J. and Rutter, W. J. (1979) Isolation of biologically active ribonucleic acid from sources enriched in ribonuclease. *Biochemistry* 18, 5294–5299.
5. Lan, M. S., Batra, S. K., Qi, W-N., Metzgar, R. S. and Hollingsworth M. A. (1990) Cloning and sequencing of a human pancreatic tumor mucin cDNA. *J. Biol. Chem.* 265, 15294–15299.
6. Batra S. K., Metzgar, R. S. and Hollingsworth, M. A. (1991) Isolation and characterization of a complementary DNA (PD-1) differentially expressed by human pancreatic ductal cell tumors. *Cell Growth Differ.* 2, 385–390.
7. Batra, S. K., Metzgar, R. S., Hollingsworth, M. A. (1991) A simple method for the construction of subtracted cDNA libraries. *Gene Analysis and Tech. Appl.* 8, 129–133.
8. Berry, R., Stevens, T. J., Walter, N. A., Wilcox, A. S., Rubano, T., Hopkins, J. A., Weber, J., Goold, R., Soares, M. B. and Sikela, J. M. (1995) Gene-based sequence-tagged-sites (STSs) as the basis for a human gene map. *Nat. Genet.* 10, 415–23.
9. Bellanne-Chantelot, C., Lacroix, B., Ougen, P., Billault, A., Beaufils, S., Bertrand, S., Georges, I., Glibert, F., Gros, I., Lucotte, G., et al. (1992) Mapping the whole human genome by fingerprinting yeast artificial chromosomes. *Cell* 70, 1059–68.
10. Wilcox, A. S., Khan, A. S., Hopkins, J. A., Sikela J. M. (1991) Use of 3' untranslated sequences of human cDNAs for rapid chromosome assignment and conversion to STSs: implications for an expression map of the genome. *Nucleic Acids Res.* 19, 1837–43.
11. Holmstrom, K., Brandt, T. and Kallesoe, T. (1994) The sequence of a 32,420 bp segment located on the right arm of chromosome II from *Saccharomyces cerevisiae*. *Yeast* 10 Suppl A, 47–S62.
12. Mackay, A. M., Eckley, D. M., Chue, C. and Earnshaw, W. C. (1993) Molecular analysis of the INCENPs (inner centromere proteins) separate domains are required for association with microtubules during interphase and with the central spindle during anaphase. *J. Cell Biol.* 123, 373–385.
13. Charles, R. S., Harrison, R. W., Bell, G. I., Pilkis, S. J. and Weber, I. T. (1994) Molecular model of human beta-cell glucokinase built by analogy to the crystal structure of yeast hexokinase B. *Diabetes*, 43, 784–91.
14. Heck, J. D. and Hatfield G. W. (1988) Valyl-tRNA synthetase gene of *Escherichia coli* K12. *J. Biol. Chem.* 263, 868–877.
15. Birolo, L., Arnone, M. I., Cubellis, M. V., Andreotti, G., Nitti, G., Marino, G. and Sannia, G. (1991) The active site of *Sulfolobus solfactaricus* aspartate aminotransferase. *Biochim. Biophys. Acta.,* 1080, 198–204.
16. McKay, D. B., Weber, I. T. and Steitz, T. A. (1982) Structure of catabolite gene activator protein at 2.9 Å resolution. Incorporation of amino acid sequence and interactions with cyclic AMP. *J. Biol. Chem.* 257, 9518–9524.
17. Clegg, C. H., Cadd, G. G. and McKnight, G. S. (1988) Genetic characterization of a brain-specific form of the type I regulatory subunit of cAMP-dependent protein kinase. *Proc. Natl. Acad. Sci., USA.* 85, 3703–3707.
18. Garcia-Bustos, J., Heitman, J., and Hall, M. N. (1991) Nuclear protein localization. *Biochem. Biophys. Acta* 1071, 83–101.
19. Lazinski, D., Grzadielska, E. and Das, A. (1989) Sequence-specific recognition of RNA hairpins by bacteriophage antiterminators requires a conserved arginine-rich motif. *Cell* 59, 207–218.
20. Benezra, R., Davis, R. L., Lockshon, D., Turner, D. L. and Weintraub, H. (1990) The protein Id: A negative regulator of helix-loop-helix DNA binding proteins. *Cell* 61, 49–59.
21. Rushlow, C. A., Hogan, A., Pinchin, S. M., Howe, K. M., Lardelli, M. and Ish-Horowicz, D. (1989) The *Drosophila* hairy protein acts in both segmentation and bristle patterning and shows homology to N-myc. *EMBO J.* 8, 3095–3103.
22. Kern, H. F., Roher, H. D., von Bulow, M. and Koppel, G. (1987) Fine structure of three major grades of malignancy of human pancreatic adenocarcinoma. *Pancreas* 2, 2–13.
23. Aitalo, K. and Schwab, M. (1986) Oncogene amplification in tumor cells. *Adv. Cancer Res.* 47, 235–281.
24. Stark G R. (1993) Regulation and mechanisms of mammalian gene amplification. *Adv Cancer Res.* 61, 87–113.
25. Griffin A. C., Hrubin R. H., Morsberger, L. A., Ellingham, T., Long, P. P., Jaffee, E. M., Hauda, K M., Bohlander S. K. and Yeo, C. J. (1995) Consistent chromosome abnormalities in adenocarcinomas of the pancreas. *Cancer Res.* 55, 2394–2399.
26. Barton, C. M., Hall, P. A., Hughes, C. M., Gullick, W. J. and Lemoine, N. R. (1991) Transforming growth factor alpha and epidermal growth factor in human pancreatic cancer. *J. Pathol.* 163, 111–116.
27. Korc, M., Chandraskar, B., Yamanaka, Y., Friess, H., Buchier, M. and Beger, H. G. (1992) Overxepression of the epidermal growth factor receptor and in human pancreatic cancer assicated with concomitant increase in levals of epidermal growth factor and transforming growth factor alpha. *J. Clin. Invest.* 90, 1352–1360.
28. Lemoine, N. R., Lobresco, M., Leung, H., Barton, C., Hughes, C. M., Prigent, S. A., Gullick, W. J. and Kloppel, G. (1992) The erB-2 oncoprotein in human pancreatic cancer. *J. Pathol.* 168, 269–273.
29. Prat, M., Narsimhan, R. P., Crepaldi, T., Nicotra, M. R., Natali, P. G and Comoglio, P. M. (1991) The receptor encoded by the human c-MET oncogene is expressed in hepatocytes, epithelial cells and soild tumors. *Int. J. Cancer* 49, 323–328.

30. Brunie, S. (1990) Crystallographic study at 2.5 Å resolution of the interaction of methionyl-tRNA synthetase from *Escherichia coli* with ATP. *J. Mol. Biol.* 216, 411–424.
31. Ford, G. C., Eichele, G. and Jansonius, J. N. (1980) Three-dimensional structure of a pyriodoxal-phosphate-dependent enzyme, mitochondrial aspartate aminotransferase. *Proc. Natl. Acad. Sci, USA* 77, 2559–2563.
32. Mehta, P. K., Hale, T. I. and Christen, P. (1989) Evolutionary relationships among aminotransferases. Tyrosine aminotransferase, histidinol-phosphate aminotransferase, and aspartate aminotransferase are homologous proteins. *Eur. J. Biochem.* 186, 249–253.
33. Barringer, M. (1991) Dimers Direct development. *Science* 251:1176–1177.
34. Murre, C., Bain, G., van-Dijk, M A., Engel, I., Furnari, B. A., Massari, M. E., Matthews, J. R., Quong, M. W., Rivera, R. R., Stuiver, M. H. (1994) Structure and function of helix-loop-helix proteins. *Biochim. Biophys. Acta,* 1218, 129–35.
35. Möller, W. and Amons, R. (1985) Phosphate-binding sequences in nucleotide-binding proteins. *FEBS* 186, 1–7.
36. Gunning, P., Leavitt, J., Muscat, G., Ng, S. and Kedes, L. (1987) A human β actin expression vector system directs high level accumulation of antisense transcripts. *Proc. Natl. Acad. Sci. USA* 84, 4831–4835.
A. Fearon, E. R. and vogelstein, B. (1990) A genetic model for colorectal tumorigenesis. *Cell* 61, 759–767.
B. Jacoby, L. B. (1993) Clonal origin of nervous system tumors. In: Levine, A. J., Schmidek, H. H., eds. Molecular genetics of nervous system tumors. Wiley-Liss, New York, p. 209–215.
C. Batra, S. K., Rasheed, B. K. A., Bigner, S. H. and Bigner, D. D. (1994) Biology of disease. Oncogenes and anti-oncogenes in human central nervous system tumors. *Lab. Invest.* 71, 621–636.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An antibody immunologically specific for an isolated human PD2 protein consisting of SEQ ID NO:2, wherein said human PD2 protein comprises an amino terminal helix-loop-helix domain and a centrally localized nuclear transport signal and nucleotide binding site.

2. The antibody of claim 1, which is a monoclonal antibody.

3. The antibody of claim 1, which is a polyclonal antibody.

4. A method for detecting human PD2 protein consisting of SEQ ID NO: 2, or a fragment thereof in a sample, comprising:

a) obtaining a sample suspected of containing the human PD2 protein or the fragment thereof;

b) contacting said sample with the antibody as claimed in claim 1, under conditions effective to allow the formation of immune complexes; and c) detecting the immune complexes so formed.

5. The method of claim 4, wherein said antibody is linked to a detectable label.

6. The method of claim 5, wherein said detectable label is selected from the group consisting of a radioactive, a fluorescent, a biological, and an enzymatic label.

7. A kit for detecting human PD2 protein consisting of SEQ ID NO:2 or a fragment thereof in a sample, said kit comprising the antibody as claimed in claim 1 and optionally said PD2 protein for use as a positive control and instructional material.

8. The kit of claim 7, wherein said antibody is linked to a detectable label.

9. The kit of claim 8, wherein said detectable label is selected from the group consisting of a radioactive, a fluorescent, a biological, and an enzymatic label.

* * * * *